US010881732B2

(12) United States Patent
Brooks et al.

(10) Patent No.: US 10,881,732 B2
(45) Date of Patent: Jan. 5, 2021

(54) ENHANCING THE THERAPEUTIC ACTIVITY OF AN IMMUNE CHECKPOINT INHIBITOR

(71) Applicant: Maine Medical Center Research Institute, Scarborough, ME (US)

(72) Inventors: Peter C. Brooks, Harpswell, ME (US); Jennifer M. Caron, Scarborough, ME (US); Liangru Contois, Yarmouth, ME (US)

(73) Assignee: Maine Medical Center Research Institute, Scarborough, ME (US)

( * ) Notice: Subject to any disclaimer, the term of this patent is extended or adjusted under 35 U.S.C. 154(b) by 239 days.

(21) Appl. No.: 15/169,863

(22) Filed: Jun. 1, 2016

(65) Prior Publication Data

US 2017/0065716 A1 Mar. 9, 2017

Related U.S. Application Data

(60) Provisional application No. 62/169,463, filed on Jun. 1, 2015.

(51) Int. Cl.
| | | |
|---|---|---|
| *A61K 39/395* | (2006.01) |
| *A61K 39/00* | (2006.01) |
| *C07K 16/18* | (2006.01) |
| *A61K 38/39* | (2006.01) |
| *C07K 14/78* | (2006.01) |
| *A61P 37/04* | (2006.01) |
| *A61P 35/00* | (2006.01) |
| *A61K 45/06* | (2006.01) |
| *C07K 16/28* | (2006.01) |

(52) U.S. Cl.
CPC .......... *A61K 39/3955* (2013.01); *A61K 38/39* (2013.01); *A61K 39/39558* (2013.01); *A61K 45/06* (2013.01); *A61P 35/00* (2018.01); *A61P 37/04* (2018.01); *C07K 14/78* (2013.01); *C07K 16/18* (2013.01); *C07K 16/2827* (2013.01); *A61K 2039/505* (2013.01); *A61K 2039/507* (2013.01); *C07K 2317/34* (2013.01); *C07K 2317/70* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,122,635 B2 | 10/2006 | Brooks et al. | |
| 7,345,151 B2 | 3/2008 | Brooks et al. | |
| 7,588,760 B2 * | 9/2009 | Brooks | A61K 31/00 424/130.1 |
| 8,025,883 B2 | 9/2011 | Brooks et al. | |
| 9,890,208 B2 | 2/2018 | Brooks et al. | |
| 2007/0048325 A1 | 3/2007 | Van et al. | |
| 2007/0259336 A1 | 11/2007 | Burbelo et al. | |
| 2007/0259817 A1 | 11/2007 | Brooks et al. | |
| 2009/0028867 A1 * | 1/2009 | Brooks | A61K 31/00 424/141.1 |
| 2013/0309250 A1 * | 11/2013 | Cogswell | C07K 16/2827 424/172.1 |

FOREIGN PATENT DOCUMENTS

| | | |
|---|---|---|
| JP | 2002-539076 A | 11/2002 |
| JP | 2016-537340 A | 12/2016 |
| WO | 00/40597 A1 | 7/2000 |
| WO | 2007/113648 A2 | 10/2007 |
| WO | 2015/070060 A1 | 5/2015 |
| WO | 2016/196560 A1 | 12/2016 |

OTHER PUBLICATIONS

Ames et al. Abstract 1549: Regulation of inflammation and tumor growth by the novel XL313 cryptic ECM element. Cancer Res Apr. 15, 2011 (71) (8 Supplement) 1549 (Year: 2011).*
Ames et al. Generation of an RGD containing soluble proinflammatory form of the XL313 cryptic collagen epitope during tumor growth and inflammation. Cancer Research 73(8 Supplement):4984-4984, Abstract 4984 (Year: 2013).*
Lipson et al. From Discovery to Development: Blocking PD-1 and its Ligands. The Melanoma Letter Summer 2013, vol. 31, No. 2, pp. 4-7 (Year: 2013).*
Menzies et al. Recent advances in melanoma systemic therapy. BRAF inhibitors, CTLA4 antibodies and beyond. European Journal of Cancer. vol. 49, Issue 15, Oct. 2013, pp. 3229-3241 (Year: 2013).*
Hamid et al. Clinical activity, safety, and biomarkers of MPOL3280A, an engineered PO-L 1 antibody in patients with locally advanced or metastatic melanoma (mM). Journal of Clinical Onoology 31, No. 15_suppl (May 20, 2013) 9010-9010. (Year: 2013).*
Menzies, Am., New systemic therapies for metastatic melanoma—MAPK inhibitors and Immunotherapy. Cancer Forum, Nov. 2012, vol. 36 pp. 1-6 (Year: 2012).*
Iwai et al. Involvement of PD-L 1 on tumor cells in the escape from host immune system and tumor immunotherapy by PD-L 1 blockade. Proc Natl Acad Sci U S A. Sep. 17, 2002;99(19):12293-7. (Year: 2002).*
Mahoney et al. Combination cancer immunotherapy and new immunomodulatory targets. Nat Rev Drug Discov. Aug. 2015;14(8): 561-84 (Year: 2014).*
Ames et al. Identification of an Endogenously Generated Cryptic Collagen Epitope (XL313) That May Selectively Regulate Angiogenesis by an Integrin Yes-associated Protein (YAP) Mechano-transduction. Journal of Biological J Biol Chem. Feb. 5, 2016; 291(6): 2731-2750 (Year: 2016).*

(Continued)

*Primary Examiner* — Maher M Haddad
(74) *Attorney, Agent, or Firm* — Mintz Levin Cohn Ferris Glovsky and Popeo, P.C.

(57) ABSTRACT

The present invention provides antagonists and methods of use thereof in the treatment of cancer and abnormal immune suppression diseases.

6 Claims, 16 Drawing Sheets

Specification includes a Sequence Listing.

(56) References Cited

OTHER PUBLICATIONS

Ames et al. The Soluble RGD-containing Cryptic Collagen, XL313, Epitope Induces Angiogenesis Through a p38MAPK Dependent Mechanism. University of Maine GSBSE, Annual Meeting Sep. 2014. pp. 10-11 (Year: 2014).*

Massi et al. PD-L1 marks a subset of melanomas with a shorter overall survival and distinct genetic and morphological characteristics. Annals of Oncology, vol. 25, Issue 12, Dec. 1, 2014, pp. 2433-2442. (Year: 2014).*

Cao et al. (Dec. 21, 2011) "Forty-Year Journey of Angiogenesis Translational Research", Science Translational Medicine, 3(114):114rv3.

Caron et al. (Jun. 2016) "Inhibition of Ovarian Tumor Growth by Targeting the HU177 Cryptic Collagen Epitope", The American Journal of Pathology, 186(6):1649-1661.

Chung et al. (Aug. 13, 1993) "A 5' Element of the Chicken β-globin Domain Serves as an Insulator in Human Erythroid Cells and Protects Against Position Effect in Drosophila", Cell, 74(3):505-514.

Rattan et al. (Nov. 1992) "Protein Synthesis, Post-translational Modifications, and Aging", Annals of the New York Academy of Sciences, 663:48-62.

Seifter et al. (1990) "Analysis for Protein Modifications and Non-protein Cofactors", Methods in Enzymology, 182:626-646.

(Jul. 29, 2019) OncoSec Receives Notice of Allowance from U.S. Patent and Trademark Office for Patent Application with Claims Covering Cytokine-Based Intratumoral Immunotherapies, Oncosec, 2 pages.

Adair-Kirk et al.(Feb. 2008) "Fragments of Extracellular Matrix as Mediators of Inflammation", The International Journal of Biochemistry & Cell Biology, 40(6-7):1101-1110.

Adler et al. (Oct. 22, 2013) "Serum Deprivation Inhibits the Transcriptional Co-Activator YAP and Cell Growth via Phosphorylation of the 130-kDa Isoform of Angiomotin by the LATS1/2 Protein Kinases", PNAS, 110(43):17368-17373.

Alghisi et al. (Feb. 12, 2009) "The Integrin Antagonist Cilengitide Activates αVβ3, Disrupts VE-Cadherin Localization at Cell Junctions and Enhances Permeability in Endothelial Cells", Plos One, 4(2):14 pages.

Atkinson (Dec. 2014) "Redefining the Role(s) of Endothelial αVβ3-Integrin in Angiogenesis", Biochemical Society Transactions, 42(6):1590-1595.

Bergers et al. (Aug. 2008) "Modes of Resistance to Anti-Angiogenic Therapy", Nature Reviews Cancer, 8 (8):592-603.

Blasi et al. (May 1990) "Immortalization of Murine Microglial Cells by a V-Raf / V-Myc Carrying Retrovirus", Journal of Neuroimmunology, 27(2-3):229-237.

Bonnans (Nov. 21, 2014) "Remodelling the Extracellular Matrix in Development and Disease", Nature Reviews Molecular Cell Biology, 15:786-801.

Brooke et al. (Jan. 2003) "Extracellular Matrix in Vascular Morphogenesis and Disease: Structure Versus Signal", Trends in Cell Biology, 13(1):51-56.

Brooks et al. (1994) "Integrin Alpha v Beta 3 Antagonists Promote Tumor Regression by Inducing Apoptosis of Angiogenic Blood Vessels", Cell, 79(7):1157-1164.

Brooks et al. (Apr. 22, 1994) "Requirement of Vascular Integrin Alpha v Beta 3 for Angiogenesis.", Science, 264 (5158):569-571.

Contois et al. (2015) "Inhibition of Tumor-Associated αVβ3 Integrin Regulates the Angiogenic Switch by Enhancing Expression of IGFBP-4 Leading to Reduced Melanoma Growth and Angiogenesis in Vivo", Angiogenesis, 18:31-46.

Contois et al. (Dec. 1, 2011) "Insulin-like Growth Factor Binding Protein-4 Differentially Inhibits Growth Factor-induced Angiogenesis", The Journal of Biological Chemistry, 287:1779-1789.

Contois et al. (Jun. 2009) "Integrins as Functional Hubs in the Regulation of Pathological Angiogenesis", Seminars in Cancer Biology, 19(5):318-328.

Cretu et al. (May 15, 2007) "Disruption of Endothelial Cell Interactions with the Novel HU177 Cryptic Collagen Epitope Inhibits Angiogenesis", Clinical Cancer Research, 3(10):3068-3078.

Dai et al. (Nov. 22, 2013) "Phosphorylation of Angiomotin by Lats1/2 Kinases Inhibits F-actin Binding, Cell Migration, and Angiogenesis", The Journal of Biological Chemistry, 288(47):34041-34051.

Danhier et al. (Sep. 11, 2012) "RGD-Based Strategies to Target Alpha(v) Beta(3) Integrin in Cancer Therapy and Diagnosis", Molecular Pharmaceutics, 9(11):2961-2973.

Davis George E. (Mar. 2011) "Angiogenesis and Proteinases: Influence on Vascular Morphogenesis, Stabilization and Regression", Drug Discovery Today Disease Models, 8(1):13-20.

Deryugina et al. (2008) "Chick Embryo Chorioallantoic Membrane Models to Quantify Angiogenesis Induced by Inflammatory and Tumor Cells or Purified Effector Molecules", Methods in enzymology, 444:21-41.

Deryugina et al. (2014) "Tissue-Infiltrating Neutrophils Constitute the Major in Vivo Source of Angiogenesis-Inducing MMP-9 in the Tumor Microenvironment", Neoplasia, 16(10):771-788.

Du et al. (May 3, 1991) "Ligands "Activate" Integrin αIIbβ3 (Platelet GPIIb-IIIa)", Cell, 65(3):409-416.

Dupont et al. (Jun. 8, 2011) "Role of YAP/TAZ in Mechanotransduction", Nature, 474:179-183.

Emens et al. (Jan. 2019) "Long-term Clinical Outcomes and Biomarker Analyses of Atezolizumab Therapy for Patients With Metastatic Triple-Negative Breast Cancer", JAMA Oncology, 5(1):74-82.

Feng et al. (2008) "The Angiogenic Response Is Dictated by β3 Integrin on Bone Marrow-derived Cells", Journal of Cell Biology, 183(6):1145-1157.

Gajewski et al. (Oct. 2013) "Innate and adaptive immune cells in the tumor microenvironment", Nature Immunology, 14(10):1014-1022.

Gangaraju et al. (2011) "Pro-Inflammatory Angiogenesis Is Mediated by p38 MAP Kinase", Journal of Cellular Physiology, 226(3):800-808.

Goepfert et al. (May 28, 2019) "Rational Combination of Parvovirus H1 With CTLA-4 and PD-1 Checkpoint Inhibitors Dampens the Tumor Induced Immune Silencing", Frontiers in Oncology, 9:12 pages.

Gong et al. (Jan. 15, 2010) "G Protein Subunit Galpha13 Binds to Integrin aIIbb3 and Mediates Integrin "Outside-In" Signaling", Science, 327:340-343.

Gong et al. (Aug. 17, 2013) "Sprouty4 Regulates Endothelial Cell Migration via Modulating Integrin β3 Stability Through C-Src", Angiogenesis, 16(4):861-875.

Govindan et al. (Oct. 20, 2017) "Phase III Trial of Ipilimumab Combined With Paclitaxel and Carboplatin in Advanced Squamous Non-Small-Cell Lung Cancer", Journal of Clinical Oncology, 35(30):3449-3457.

Grabosch et al. (Mar. 2019) "Cisplatin-Induced Immune Modulation in Ovarian Cancer Mouse Models with Distinct Inflammation Profiles", Oncogene, 38(13):2380-2393.

Greenberg et al. (Nov. 9, 2008) "A Role for VEGF as a Negative Regulator of Pericyte Function and Vessel Maturation", Nature, 456(7223):809-813.

Gurrath et al. (Oct. 1, 1992) "Conformation/activity Studies of Rationally Designed Potent Anti-Adhesive RGD Peptides", European Journal of Biochemistry, 210(3):911-921.

Hangai et al. (Oct. 1, 2002) "Matrix Metalloproteinase-9-Dependent Exposure of a Cryptic Migratory Control Site in Collagen Is Required Before Retinal Angiogenesis", The American Journal of Pathology, 161(4):1429-1437.

Herbst et al. (Nov. 27, 2014) "Predictive Correlates of Response to the Anti-PD-L1 Antibody MPDL3280A in Cancer Patients", Nature, 515(7528):563-567.

Hersey et al. (Mar. 15, 2010) "A Randomized Phase 2 Study of Etaracizumab, a Monoclonal Antibody Against Integrin αVβ3, ± Dacarbazine in Patients with Stage IV Metastatic Melanoma", Cancer, 116(6):1526-1534.

Hodivala-Dilke et al. (2008) "AlphavBeta3 Integrin and Angiogenesis: A Moody Integrin in a Changing Environment", Current Opinion in Cell Biology, 20:514-519.

(56) References Cited

OTHER PUBLICATIONS

Jetten et al. (2014) "Anti-Inflammatory M2, but Not Pro-Inflammatory M1 Macrophages Promote Angiogenesis in Vivo", Angiogenesis, 17(1):109-118.
Johnson et al. (Dec. 13, 2013) "The Two Faces of Hippo: Targeting the Hippo Pathway for Regenerative Medicine and Cancer Treatment", Nature Reviews Drug Discovery, 13:63-79.
Kaneko et al. (May 2, 2014) "Integrin αV in the Mechanical Response of Osteoblast Lineage Cells", Biochemical and Biophysical Research Communications, 447(2):352-357.
Keilholz et al. (2019) "Avelumab in Patients with Previously Treated Metastatic Melanoma: Phase 1 B Results from the Javelin Solid Tumor Trial", Journal for !mmunoTherapy of Cancer, 7(1):13 pages.
Kostidis et al. (Aug. 1, 2004) "The Relative Orientation of the Arg and Asp Side Chains Defined by a Pseudodihedral Angle as a Key Criterion for Evaluating the Structure-Activity Relationship of RGD Peptides", Journal of Peptide Science, 10(8):494-509.
Kostine et al. (2018) "Rheumatic Disorders Associated with Immune Checkpoint Inhibitors in Patients with Cancer-· Clinical Aspects and Relationship with Tumour Response: A Single-Centre Prospective Cohort Study", Annals of the Rheumatic Diseases, 77(3):393-398.
Kunicki et al. (Feb. 14, 1997) "Molecular Determinants of Arg-Gly-Asp Ligand Specificity for (β3 Integrins", The Journal of Biological Chemistry, 272:4103-4107.
Legler et al. (2001) "Superactivation of Integrin (α)V(β)3 by Low Antagonist Concentrations", Journal of Cell Science, 114:1545-1553.
Liao et al. (Jan. 13, 2015) "Interaction of Kindlin-2 with Integrin β3 Promotes Outside-in Signaling Responses by the αVβ3 Vitronectin Receptor", Blood, 125(12):1995-2004.
Long et al. (Aug. 1, 2019) "Epacadostat plus Pembrolizumab Versus Placebo plus Pembrolizumab in Patients with Unresectable or Metastatic Melanoma (ECH0-301/Keynote-252): A Phase 3, Randomised, Double-Blind Study", The Lancet Oncology, 20(8):1083-1097.
Madsen et al. (Sep. 9, 2013) "M2-like Macrophages Are Responsible for Collagen Degradation Through a Mannose Receptor-mediated Pathway", The Journal of Cell Biology, 202(6):951-966.
Massard et al. (Sep. 10, 2016) "Safety and Efficacy of Durvalumab (MEDI4736), an Anti-Programmed Cell Death Ligand-l Immune Checkpoint Inhibitor, in Patients With Advanced Urothelial Bladder Cancer", Journal of Clinical Oncology, 34(26):3119-3125.
Mateos et al. (Sep. 2019) "Pembrolizumab plus Pomalidomide and Dexamethasone for Patients with Relapsed or Refractory Multiple Myeloma (Keynote-183): A Randomised, Open-Label, Phase 3 Trial", The Lancet Haematology, 6(9):e459-e469.
Matsumoto et al. (Jan. 7, 2002) "p38 MAP Kinase Negatively Regulates Endothelial Cell Survival, Proliferation, and Differentiation in FGF-2-stimulated Angiogenesis", The Journal of Cell Biology, 156(1):149-160.
Mcmullen et al. (Dec. 15, 2003) "Vascular Endothelial Growth Factor-Mediated Activation of P38 Is Dependent upon Src and RAFTK/Pyk2", Oncogene, 23:1275-1282.
Mitra et al. (Oct. 2006) "Integrin-Regulated FAK—SRC Signaling in Normal and Cancer Cells", Current Opinion in Cell Biology, 18(5):516-523.
Miyoshi et al. (Sep. 2006) "Tumor-Specific Expression of the RGD-α3(IV)NC1 Domain Suppresses Endothelial Tube Formation and Tumor Growth in Mice", The Faseb Journal, 20(11):1264-1275.
Mogford et al. (1996) "Vascular Smooth Muscle Alpha v Beta 3 Integrin Mediates Arteriolar Vasodilation in Response to RGD Peptides", Circulation Research, 79(4):821-826.
Montgomery et al. (Sep. 13, 1994) "Integrin Alpha v Beta 3 Rescues Melanoma Cells from Apoptosis in Three-Dimensional Dermal Collagen", PNAS, 91(19):8856-8860.
Moserle et al. (Jan. 2014) "Antiangiogenic Therapies: Going beyond Their Limits", Cancer Discovery, 4 (1):31-41.
Petitclerc et al. (Mar. 17, 2000) "New Functions for Non-collagenous Domains of Human Collagen Type IV: Novel Integrin Ligands Inhibiting Angiogenesis and Tumour Growth InVivo", The Journal of Biological Chemistry, 275 (11):8051-8061.
Pickup et al. (Dec. 1, 2014) "The Extracellular Matrix Modulates the Hallmarks of Cancer", EMBO Reports, 15 (12):1243-1253.
Pierschbacher (Dec. 25, 1987) "Influence of Stereochemistry of the Sequence Arg-Gly-Asp-Xaa on Binding Specificity in Cell Adhesion", The Journal of Biological Chemistry, 262(36):17294-17298.
Reynolds et al. (Jan. 1, 2002) "Enhanced Pathological Angiogenesis in Mice Lacking beta3 Integrin or beta3 and beta5 Integrins", Nature Medicine, 8(1):27-34.
Reynolds et al. (Mar. 22, 2009) "Stimulation of Tumor Growth and Angiogenesis by Low Concentrations of RGD-Mimetic Integrin Inhibitors", Nature Medicine, 15(4):392-400.
Robinson et al. (Oct. 2011) "The Role of β3-Integrins in Tumor Angiogenesis: Context Is Everything", Current Opinion in Cell Biology, 23(5):630-637.
Rousseau et al. (1997) "p38 MAP Kinase Activation by Vascular Endothelial Growth Factor Mediates Actin Reorganization and Cell Migration in Human Endothelial Cells", Oncogene, 15(18):2169-2177.
Ruoslahti (Nov. 1996) "RGD and Other Recognition Sequences for Intergrins", Annual Review of Cell and Developmental Biology, 12:697-715.
Schnoor et al. (2008) "Production of Type VI Collagen by Human Macrophages: A New Dimension in Macrophage Functional Heterogeneity", Journal of immunology, 180(8):5707-5719.
Shen et al. (Oct. 2012) "Inside-Out, Outside-In, and Inside-Outside-In: G Protein Signaling in Integrin-Mediated Cell Adhesion, Spreading, and Retraction", Current Opinion in Cell Biology, 24(5):600-606.
Shen et al. (Jan. 30, 2015) "YAP Regulates S-Phase Entry in Endothelial Cells", Plos One, 10(1):19 pages.
Skjot-Arkil et al. (2010) "Macrophage-Mediated Proteolytic Remodeling of the Extracellular Matrix in Atherosclerosis Results in Neoepitopes: A Potential New Class of Biochemical Markers", Assay and Drug Development Technologies, 8(5):542-552.
Somanath et al. (2009) "Cooperation Between Integrin αvβ3 and VEGFR2 in Angiogenesis", Angiogenesis, 12 (2):177-185.
Steri et al. (Jan. 3, 2014) "Acute Depletion of Endothelial β3-Integrin Transiently Inhibits Tumor Growth and Angiogenesis in Mice", Circulation Research, 114(1):79-91.
Stupp et al. (Sep. 2014) "Cilengitide Combined with Standard Treatment for Patients with Newly Diagnosed Glioblastoma with Methylated MGMT Promoter (Centric EORTC 26071-22072 Study): A Multicentre, Randomised, Open-Label, Phase 3 Trial", The Lancet Oncology, 15(10):1100-1108.
Sudhakar (Apr. 15, 2003) "Human Tumstatin and Human Endostatin Exhibit Distinct Antiangiogenic Activities Mediated by αvβ3 and α5β1 Integrins", PNAS, 100(8):4766-4771.
Tang et al. (2013) "MT1-MMP-Dependent Control of Skeletal Stem Cell Commitment via a β1-integrin/YAP/TAZ Signaling Axis", Developmental Cell, 25(4):402-416.
Tran et al. (Nov. 2, 2017) "Cisplatin Alters Antitumor Immunity and Synergizes with PD-1/PD-LI Inhibition in Head and Neck Squamous Cell Carcinoma", Cancer Immunology Research, 5(12):1141-1151.
Von Wichert et al. (Apr. 14, 2003) "RPTP-αActs as a Transducer of Mechanical Force on αV/β3-Integrin—cytoskeleton Linkages", The Journal of Cell Biology, 161(1):143-153.
Wang et al. (Sep. 16, 2019) "HPV-Positive Status Associated with Inflamed Immune Microenvironment and Improved Response to Anti-PD-1 Therapy in Head and Neck Squamous Cell • Carcinoma", Scientific Reports, 13404, 9:10 pages.
Xu et al. (Sep. 3, 2001) "Proteolytic Exposure of a Cryptic Site Within Collagen Type IV Is Required for Angiogenesis and Tumor Growth in Vivo", The Journal of Cell Biology, 154(5):1069-1079.
Yip et al. (Nov. 1, 1997) "An Arg-Gly-Asp Peptide Stimulates Constriction in Rat Afferent Arteriole", The American Journal of Physiology, 273(5):F768-776.
Yu et al. (Dec. 20, 2011) "Early Integrin Binding to Arg-Gly-Asp Peptide Activates Actin Polymerization and Contractile Movement That Stimulates Outward Translocation", PNAS, 108(51):20585-20590.

(56) References Cited

OTHER PUBLICATIONS

Zwadlo-Klarwasser et al. (Mar. 2001) "The Chorioallantoic Membrane of the Chick Embryo as a Simple Model for the Study of the Angiogenic and Inflammatory Response to Biomaterials", Journal of Materials Science: Materials in Medicine, 12:195-199.

* cited by examiner

FIG. 3A

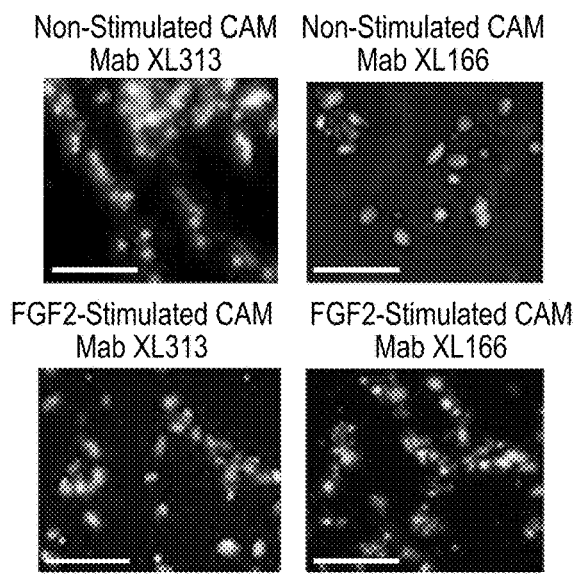

Non-Stimulated CAM Mab XL313 | Non-Stimulated CAM Mab XL166
FGF2-Stimulated CAM Mab XL313 | FGF2-Stimulated CAM Mab XL166

FIG. 3C

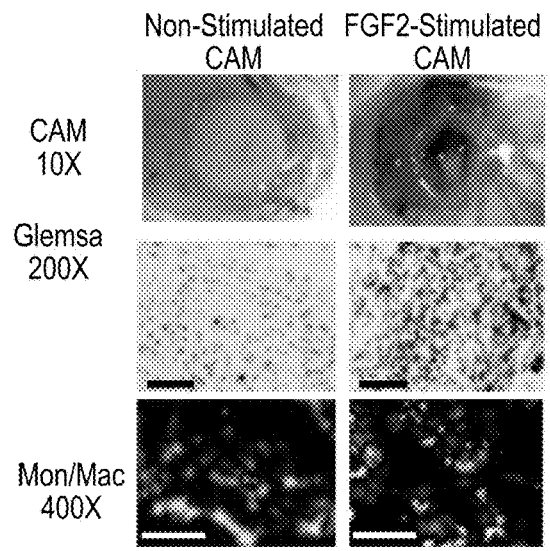

Non-Stimulated CAM | FGF2-Stimulated CAM
CAM 10X
Glemsa 200X
Mon/Mac 400X

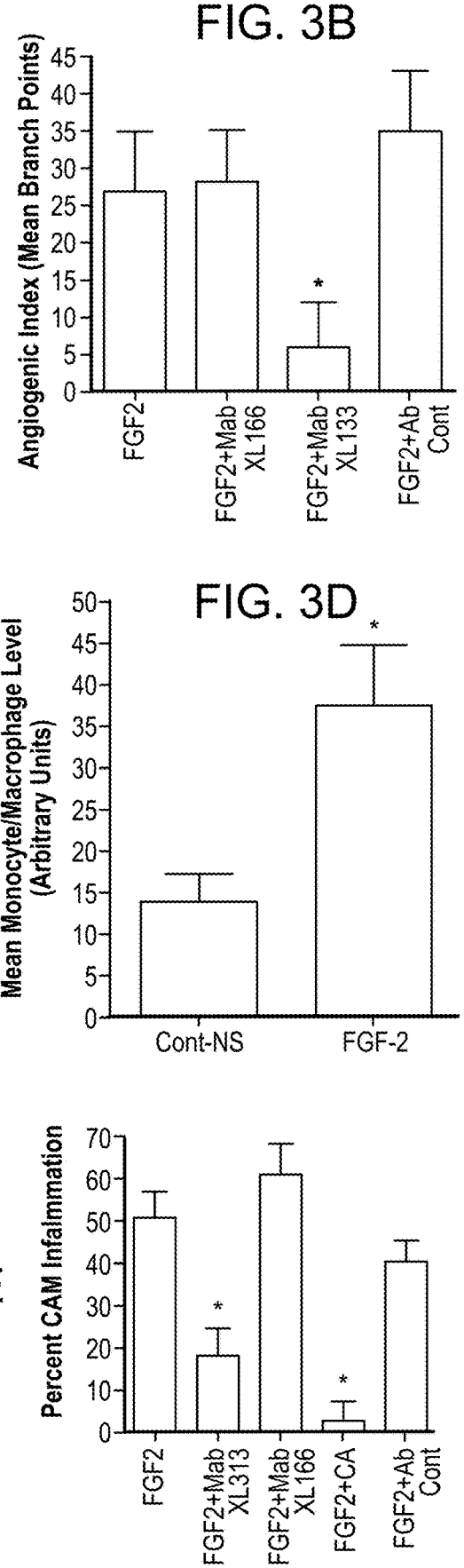

FIG. 3B — Angiogenic Index (Mean Branch Points) vs FGF2, FGF2+Mab XL166, FGF2+Mab XL133, FGF2+Ab Cont FIG. 3D — Mean Monocyte/Macrophage Level (Arbitrary Units) vs Cont-NS, FGF-2

FIG. 3E — Percent CAM Infalmmation vs FGF2, FGF2+Mab XL313, FGF2+Mab XL166, FGF2+CA, FGF2+Ab Cont FIG. 4A
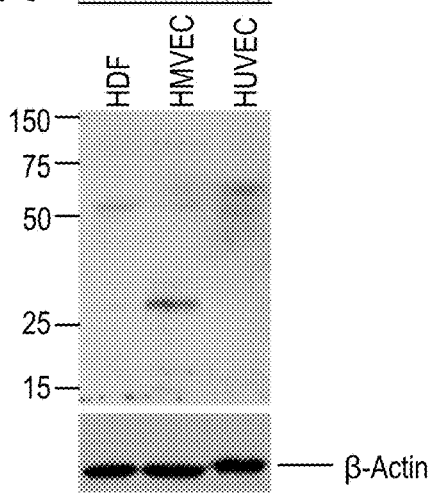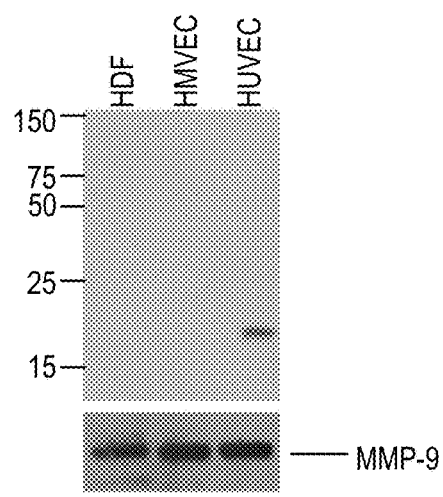
FIG. 4B
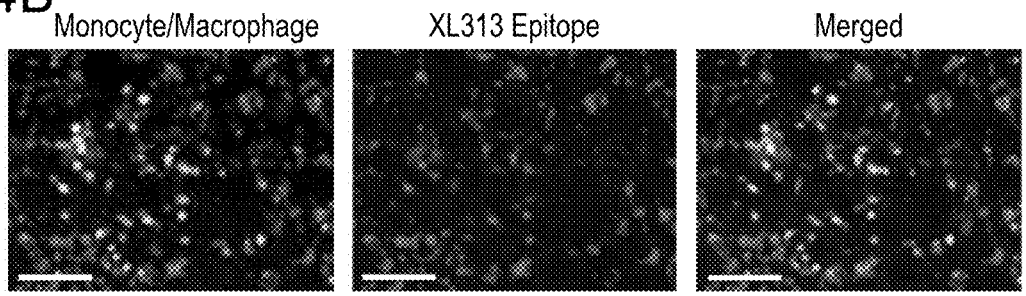
FIG. 4C
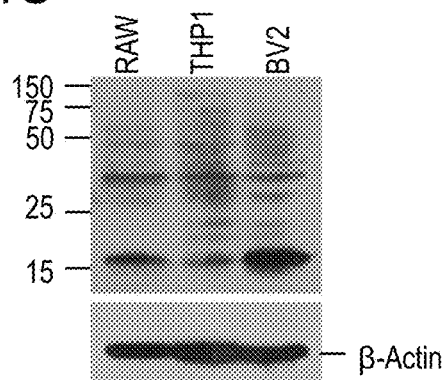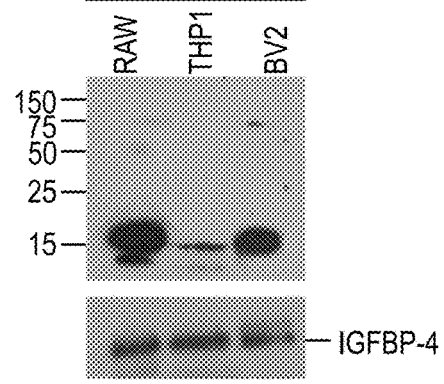
FIG. 4D
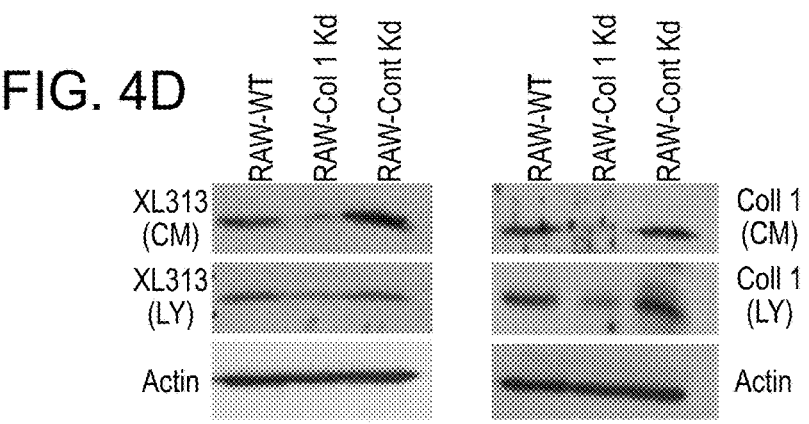

B16F10 Melanoma

M21 Melanoma (24hrs)

CCL-49 Melanoma (1hrs)

HUVEC (24hrs)

ENHANCING THE THERAPEUTIC ACTIVITY OF AN IMMUNE CHECKPOINT INHIBITOR

RELATED APPLICATIONS

This application claims the benefit of priority under 35 U.S.C. § 119(e) to U.S. Provisional Application No. 62/169,463, filed Jun. 1, 2015, which is incorporated herein by reference in its entirety.

GOVERNMENT SUPPORT

This invention was made with government support under grant numbers CA091645, HL065301, HL083151, RR015555, GM103392, and RR0181789 awarded by the National Institutes of Health. The government has certain rights in the invention.

BACKGROUND OF THE INVENTION

Extracellular matrix (ECM) remodeling regulates angiogenesis. However, prior to the invention described herein, the precise mechanisms by which structural changes in ECM proteins contribute to angiogenesis were not fully understood. The role of integrin αvβ3 in angiogenesis is complex, as evidence exists for both positive and negative functions. As such, prior to the invention described herein, there was a pressing need to develop an understanding of the role of integrin αvβ3 in angiogenesis.

SUMMARY OF THE INVENTION

The invention is based, in part, upon the surprising discovery that an antagonist (i.e., Mab XL313) specifically directed to a cryptic RGDKGE (SEQ ID NO.1)-containing collagen epitope significantly enhanced the anti-tumor efficacy of an antibody that targets the immune checkpoint regulatory protein, PDL-1. Additionally, the invention is based, in part, on an antagonist of integrin αvβ3 that is used to enhance the therapeutic activity of an immune checkpoint inhibitor, e.g., cytotoxic T-lymphocyte-associated protein 4 (CTLA-4), programmed death ligand-1 (PDL-1), programmed cell death protein 1 (PD-1), lymphocyte-activation gene 3 (Lag3), leukocyte-associated immunoglobulin-like receptor 1 (LAIR1) and/or leukocyte-associated immunoglobulin-like receptor 2 (LAIR2) antibodies.

The present invention features compositions and methods for treating cancer and diseases characterized by abnormal immune suppression. For example, methods of treating cancer in a subject are carried out by identifying a subject, e.g., a human subject, that has been diagnosed with cancer; administering an immune checkpoint inhibitor; and administering an antagonist of collagen or a fragment thereof, thereby treating cancer in the subject. In some cases, the immune checkpoint inhibitor comprises an inhibitor of CTLA-4, PDL-1, PD-1, CTLA-4, Lag3, LAIR1 and/or LAIR2. For example, the inhibitor of PDL-1 comprises a PDL-1 antibody.

Suitable types of collagen include collagen type-I, collagen type-II, collagen type-III and collagen type-IV (e.g., the alpha 6 chain of collagen type-IV). In some cases, the antagonist of collagen or a fragment thereof comprises an antagonist of the XL313 cryptic collagen epitope. For example, the antagonist comprises an antibody that binds a cryptic RGDKGE (SEQ ID NO. 1) containing collagen epitope. Preferably, the antibody comprises a monoclonal antibody, e.g., an XL313 monoclonal antibody.

Preferably, the antagonist of collagen or a fragment thereof enhances anti-tumor activity of the immune checkpoint inhibitor and inhibits an inflammatory condition. Exemplary inflammatory conditions include dermatitis, pneumonitis, or colitis.

The methods described herein can be used in conjunction with one or more chemotherapeutic or anti-neoplastic agents. In some cases, the additional chemotherapeutic agent is radiotherapy. In some cases, the chemotherapeutic agent is a cell death-inducing agent.

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

Exemplary cancers are selected from the group comprising of melanoma, central nervous system (CNS) cancer, CNS germ cell tumor, lung cancer, leukemia, multiple myeloma, renal cancer, malignant glioma, medulloblatoma, breast cancer, ovarian cancer, prostate cancer, bladder cancer, fibrosarcoma, pancreatic cancer, gastric cancer, head and neck cancer, colorectal cancer. For example, a cancer cell is derived from a solid cancer or hematological cancer. The hematological cancer is, e.g., a leukemia or a lymphoma. A leukemia is acute lymphoblastic leukemia (ALL), acute myelogenous leukemia (AML), chronic lymphocytic leukemia (CLL), small lymphocytic lymphoma (SLL), chronic myelogenous leukemia (CML), or acute monocytic leukemia (AMoL). A lymphoma is follicular lymphoma, Hodgkin's lymphoma (e.g., Nodular sclerosing subtype, mixed-cellularity subtype, lymphocyte-rich subtype, or lymphocyte depleted subtype), or Non-Hodgkin's lymphoma. Exemplary solid cancers include but are not limited to melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), breast cancer (e.g., triple negative breast cancer), and lung cancer (e.g., non-small cell lung cancer).

Human dosage amounts can initially be determined by extrapolating from the amount of compound used in mice or nonhuman primates, as a skilled artisan recognizes it is routine in the art to modify the dosage for humans compared to animal models. In certain embodiments, it is envisioned that the dosage of the antagonist to collagen may vary from between about 0.1 µg compound/kg body weight to about 25000 µg compound/kg body weight; or from about 1 µg/kg body weight to about 4000 µg/kg body weight or from about 10 µg/kg body weight to about 3000 µg/kg body weight. In other embodiments this dose may be about 0.1, 0.3, 0.5, 1, 3, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000, 5500, 6000, 6500, 7000, 7500, 8000, 8500, 9000, 9500, 10000, 10500, 1100, 11500, 12000, 12500, 13000, 13500, 14000, 14500, 15000, 15500, 16000, 16500, 17000, 17500, 18000, 18500, 19000, 19500, 20000, 20500, 21000, 21500, 22000, 22500, 23000, 23500, 24000, 24500, or 25000 µg/kg body weight. In other embodiments, it is envisaged that doses may be in the range of about 0.5 µg compound/kg body weight to about 20 µg compound/kg body weight. In other embodiments, the doses may be about 0.5, 1, 3, 6, 10, or 20 mg/kg body weight. Of course, this dosage amount may be adjusted upward or downward, as is routinely done in such treatment protocols, depending on the results of the initial clinical trials and the needs of a particular patient.

In some cases, the immune checkpoint inhibitor, e.g., the inhibitor of PDL-1, is administered at a dosage of 0.01-10 mg/kg (e.g., 0.01, 0.05, 0.1, 0.5, 1, 5, or 10 mg/kg) bodyweight. For example, the PDL-1 inhibitor is administered in an amount of 0.01-30 mg (e.g., 0.01, 0.05, 0.1, 0.5, 1, 5, 10, 20, or 30 mg) per dose. In another example, the immune checkpoint inhibitor, e.g., the anti-PD-L1 antibody, is administered in the dose range of 0.1 mg/kg to 10 mg/kg of body weight. In some cases, the XL313 antibody is administered at a dosage of 0.01-10 mg/kg (e.g., 0.01, 0.05, 0.1, 0.5, 1, 5, or 10 mg/kg) bodyweight. For example, the XL313 antibody is administered in an amount of 0.01-30 mg (e.g., 0.01, 0.05, 0.1, 0.5, 1, 5, 10, 20, or 30 mg) per dose. For example, the dose range of Mab X1313 is from 0.1 mg/kg to 25 mg/kg of body weight.

The compositions of the invention (e.g., inhibitor of PDL-1 and XL313 antibody) are administered once per month, twice per month (i.e., every two weeks), every week, once per day, twice per day, every 12 hours, every 8 hours, every 4 hours, every 2 hours or every hour. The compositions of the invention (e.g., inhibitor of PDL-1 and XL313 antibody) are administered for a duration of 1 day, 2 days, 3 days, 4 days, 5 days, 6 days, 7 days, 2 weeks, 3 weeks, 4 weeks, five weeks, six weeks, 2 months, 3 months, 4 months, 5 months, 6 months, 7 months, 8 months, 9 months, 10 months, 11 months, 12 months, 2 years, 3 years, 4 years, 5 years or more. For example, the composition of the invention (e.g., inhibitor of PD-L1 and XL313 antibody) are administered one dose every two weeks for 4 to 6 weeks or until the disease is treated.

Also provided is a method of treating a disease characterized by abnormal immune suppression in a subject by identifying a subject, e.g., a human, that has been diagnosed with a disease characterized by abnormal immune suppression, administering an immune checkpoint inhibitor, and administering an antagonist of an integrin, thereby treating in the subject.

Suitable immune checkpoint inhibitors comprise an inhibitor of CTLA-4, PD-1, PDL-1, Lag3, LAIR1, or LAIR 2. For example, the immune checkpoint inhibitor comprises a CTLA-4 antibody, a PD-1 antibody, a PDL-1 antibody, a Lag3 antibody, a LAIR1 antibody, or a LAIR 2 antibody.

Preferably, the integrin comprises integrin αvβ3. For example, the antagonist of integrin αvβ3 comprises an antibody targeting αvβ3 binding RGDKGE (SEQ ID NO: 1) containing collagen epitope.

The methods described herein can be used in conjunction with one or more chemotherapeutic or anti-neoplastic agents. In some cases, the additional chemotherapeutic agent is radiotherapy. In some cases, the chemotherapeutic agent is a cell death-inducing agent.

Suitable diseases characterized by abnormal immune suppression include Type I diabetes, lupus, psoriasis, scleroderma, hemolytic anemia, vasculitis, Graves' disease, rheumatoid arthritis, multiple sclerosis, Hashimoto's thyroiditis, Myasthenia gravis, and vasculitis In some cases, the immune checkpoint inhibitor (e.g., CTLA-4 antibody, a PD-1 antibody, a PDL-1 antibody, Lag3, LAIR1, or LAIR 2) is administered at a dosage of 0.01-10 mg/kg (e.g., 0.01, 0.05, 0.1, 0.5, 1, 5, or 10 mg/kg) bodyweight. For example, the PDL-1 inhibitor is administered in an amount of 0.01-30 mg (e.g., 0.01, 0.05, 0.1, 0.5, 1, 5, 10, 20, or 30 mg) per dose. In another example, the antibody is administered in the dose range of 0.1 mg/kg to 10 mg/kg of body weight. In some cases, the antagonist of integrin αvβ3 is administered at a dosage of 0.01-10 mg/kg (e.g., 0.01, 0.05, 0.1, 0.5, 1, 5, or 10 mg/kg) bodyweight. In some cases, the XL313 antibody is administered in an amount of 0.01-30 mg (e.g., 0.01, 0.05, 0.1, 0.5, 1, 5, 10, 20, or 30 mg) per dose.

The compositions of the invention (e.g., immune checkpoint inhibitor and antagonist of integrin αvβ3) are administered once per month, twice per month (once every two weeks), once a week, once per day, twice per day, every 12 hours, every 8 hours, every 4 hours, every 2 hours or every hour. The compositions of the invention (e.g., inhibitor of PDL-1 and XL313 antibody) are administered for a duration of 1 day, 2 days, 3 days, 4 days, 5 days, 6 days, 7 days, 2 weeks, 3 weeks, 4 weeks, 2 months, 3 months, 4 months, 5 months, 6 months, 7 months, 8 months, 9 months, 10 months, 11 months, 12 months, 2 years, 3 years, 4 years, 5 years or more. The composition of the invention (e.g., inhibitor of PDL-1 and XL313 antibody) are administered one dose every two weeks for 4 to 6 weeks or until the disease is treated Also provided is a method of treating a disease characterized by an overactive immune response (e.g., an autoimmune disease) in a subject, e.g., a human subject, that has been diagnosed with an overactive immune response by administering a peptide comprising collagen or a fragment thereof, thereby treating overactive immune response in the subject. Suitable types of collagen include collagen type-I, collagen type II, collagen type III, and collagen type-IV (e.g., the alpha 6 chain of collagen type-IV). For example, the peptide comprises RGDKGE (SEQ ID NO. 1).

In some cases, the autoimmune disease comprises Graves' disease, Hashimoto's thyroiditis, Systemic lupus erythematosus (lupus), Type 1 diabetes, multiple sclerosis or rheumatoid arthritis.

Methods for healing a wound in a subject, e.g., a human subject with a wound, are carried out by administering a peptide comprising collagen or a fragment thereof to the wound of the subject, thereby healing a wound in the subject. For example, the peptide is administered to a site that is about 0.1 mm, 0.5 mm, 1 mm, 2.5 mm, 5 mm, 10 mm, 15 mm, 20 mm, or 40 mm away from a perimeter or margin of the wound. Alternatively, the peptide is administered directly to the wound itself.

Suitable types of collagen include collagen type-I, collagen type II, collagen type III, and collagen type-IV (e.g., the alpha 6 chain of collagen type-IV). For example, the peptide comprises RGDKGE (SEQ ID NO. 1).

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "antibody" is meant any immunoglobulin polypeptide, or fragment thereof, having immunogen binding ability. As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies, and the like, as well as synthetic antigen-binding peptides and polypeptides, are also included. Non-human antibodies may be humanized by grafting non-human CDRs onto human framework and constant regions, or by incorporating the entire non-human variable domains. In certain preferred embodiments, humanized antibodies may retain non-human residues within the human variable region framework domains to enhance proper binding characteristics.

"Antigenic fragment" and the like are understood as at least that portion of a peptide capable of inducing an immune response in a subject, or being able to be specifically bound by an antibody raised against the antigenic fragment. Typically, antigenic fragments are at least 7 amino acids in length. Antigenic fragments can include deletions of the amino acid sequence from the N-terminus or the C-terminus, or both. For example, an antigenic fragment can have an N- and/or a C-terminal deletion of about 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, or more amino acids. Antigenic fragments can also include one or more internal deletions of the same exemplary lengths. Antigenic fragments can also include one or more point mutations, particularly conservative point mutations. At least an antigenic fragment of protein can include the full length, wild-type sequence of the antigen. An antigenic fragment can include more than one potential antibody binding site. An antigenic fragment can be used to make antibodies for use in any of the methods provided herein.

By "autoimmune disease" is meant a disease characterized by a dysfunction in the immune system. The disease is characterized by the components of the immune system affected, whether the immune system is overactive or underactive, or whether the condition is congenital or acquired. In most cases, the disorder causes abnormally low activity or over activity of the immune system. In cases of immune system over activity, the body attacks and damages its own tissues (autoimmune). Immune deficiency diseases decrease the body's ability to fight invaders, causing vulnerability to infections. In response to an unknown trigger, the immune system may begin producing antibodies that instead of fighting infections, attack the body's own tissues. Treatment for autoimmune diseases generally focuses on reducing immune system activity.

By "blood vessel formation" is meant the dynamic process that includes one or more steps of blood vessel development and/or maturation, such as angiogenesis, arteriogenesis, vasculogenesis, formation of an immature blood vessel network, blood vessel remodeling, blood vessel stabilization, blood vessel maturation, blood vessel differentiation, or establishment of a functional blood vessel network.

By "blood vessel remodeling" or "vascular remodeling" is meant the dynamic process of blood vessel enlargement in shape and size to maintain the luminal orifice and blood flow. For example, vascular remodeling includes change in arterial size to adapt to plaque accumulation, effectively maintaining the lumen and blood flow to the myocardium.

As used herein, "binding" or "specific binding" is understood as having at least a $10^3$ or more, preferably $10^4$ or more, preferably $10^5$ or more, preferably $10^6$ or more preference for binding to a specific binding partner as compared to a non-specific binding partner (e.g., binding an antigen to a sample known to contain the cognate antibody).

By "cancer" is meant, comprising of but not limited to melanoma, central nervous system (CNS) cancer, CNS germ cell tumor, lung cancer, leukemia, multiple myeloma, renal cancer, malignant glioma, medulloblatoma, breast cancer, ovarian cancer, prostate cancer, bladder cancer, fibrosarcoma, pancreatic cancer, gastric cancer, head and neck cancer, colorectal cancer. For example, a cancer cell is derived from a solid cancer or hematological cancer. The hematological cancer is, e.g., a leukemia or a lymphoma. A leukemia is acute lymphoblastic leukemia (ALL), acute myelogenous leukemia (AML), chronic lymphocytic leukemia (CLL), small lymphocytic lymphoma (SLL), chronic myelogenous leukemia (CML), or acute monocytic leukemia (AMoL). A lymphoma is follicular lymphoma, Hodgkin's lymphoma (e.g., Nodular sclerosing subtype, mixed-cellularity subtype, lymphocyte-rich subtype, or lymphocyte depleted subtype), or Non-Hodgkin's lymphoma. Exemplary solid cancers include but are not limited to melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), breast cancer (e.g., triple negative breast cancer), and lung cancer (e.g., non-small cell lung cancer).

By "control" or "reference" is meant a standard of comparison. As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection the amount and measurement of the change can vary. Determination of statistical significance is within the ability of those skilled in the art, e.g., the number of standard deviations from the mean that constitute a positive result.

By "cryptic" is meant that a motif may be inaccessible to cell surface receptors, and once the target protein is proteolyzed or denatured, a sequence becomes exposed or generates a fragment that is then recognized by the antibody. For example, the XL313 epitope, i.e., RGDKGE core sequence within collagen type-I is cryptic in that the antibody does not react with normal collagen in its triple helical state, but once it is proteolyzed or denatured, the sequence becomes exposed or generates a fragment of collagen that is recognized by MabXL313.

As used herein, "detecting", "detection" and the like are understood that an assay performed for identification of a specific analyte in a sample, e.g., an antigen in a sample or the level of an antigen in a sample. The amount of analyte or activity detected in the sample can be none or below the level of detection of the assay or method.

By "diagnosing" and the like as used herein refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. Diagnostic methods provide an indicator that a disease is or is not present. A single diagnostic test typically does not provide a definitive conclusion regarding the disease state of the subject being tested.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "polynucleotide" or "nucleic acid" as used herein designates mRNA, RNA, cRNA, cDNA or DNA. As used herein, a "nucleic acid encoding a polypeptide" is understood as any possible nucleic acid that upon (transcription and) translation would result in a polypeptide of the desired sequence. The degeneracy of the nucleic acid code is well understood. Further, it is well known that various organisms have preferred codon usage, etc. Determination of a nucleic acid sequence to encode any polypeptide is well within the ability of those of skill in the art.

As used herein, "immunoassay" is understood as any antibody base detection method including, but not limited to enzyme linked immunosorbent assay (ELISA), radioimmune assay (RIA), Western blot, immunohistochemistry, immunoprecipitation assay such as Luciferase Immunoprecipitation System (LIPS see, e.g., US Patent Publication 2007/0259336 which is incorporated herein by reference). In a preferred embodiment, the immunoassay is a quantitative. Antibodies for use in immunoassays include any monoclonal or polyclonal antibody appropriate for use in the specific immunoassay.

By "inhibitory nucleic acid molecule" is meant a polynucleotide that disrupts the expression of a target nucleic acid molecule or an encoded polypeptide. Exemplary inhibitory nucleic acid molecules include, but are not limited to, shRNAs, siRNAs, antisense nucleic acid molecules, and analogs thereof.

As used herein, "isolated" or "purified" when used in reference to a polypeptide means that a naturally polypeptide or protein has been removed from its normal physiological environment (e.g., protein isolated from plasma or tissue, optionally bound to another protein) or is synthesized in a non-natural environment (e.g., artificially synthesized in an in vitro translation system or using chemical synthesis). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. An isolated virus or viral vector is a virus that is removed from the cells, typically in culture, in which the virus was produced.

As used herein, "kits" are understood to contain at least one non-standard laboratory reagent for use in the methods of the invention in appropriate packaging, optionally containing instructions for use. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

As used herein, "obtaining" is understood herein as manufacturing, purchasing, or otherwise coming into possession of.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Formulations of the present invention include those suitable for oral, nasal, topical, transdermal, buccal, sublingual, intramuscular, intracardiac, intraperotineal, intrathecal, intracranial, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments). Optionally the peptide further includes one or more modifications such as modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins, Structure and Molecular Properties, 2nd ed., T. E. Creighton, W.H. Freeman and Company, New York (1993); Posttranslational Covalent Modification of Proteins, B. C. Johnson, ed., Academic Press, New York, pgs. 1-12 (1983); Seifter et al., Meth. Enzymol 182:626-646 (1990); Rattan et al., Ann. N.Y. Acad. Sci. 663:48-62 (1992)).

The term "reduce" or "increase" is meant to alter negatively or positively, respectively, by at least 5%. An alteration may be by 5%, 10%, 25%, 30%, 50%, 75%, or even by 100%.

As used herein, a "reporter protein" or a "reporter polypeptide" is understood as a polypeptide that can be readily detected, preferably quantitatively detected, either directly or indirectly. A reporter polypeptide typically has an enzymatic activity, luciferase activity, alkaline phosphatase activity, beta-galactosidase activity, acetyl transferase activity, etc. wherein catalysis of a reaction with the substrate by the enzyme results in the production of a product, e.g., light, a product that can be detected at a specific wavelength of light, radioactivity, such that the amount of the reporter peptide can be determined in the sample, either as a relative amount, or as an absolute amount by comparison to control samples.

A "sample" as used herein refers to a biological material that is isolated from its environment (e.g., blood or tissue from an animal, cells, or conditioned media from tissue culture) and is suspected of containing, or known to contain an analyte, such as a protein. A sample can also be a partially purified fraction of a tissue or bodily fluid. A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

"Sensitivity and specificity" are statistical measures of the performance of a binary classification test. The sensitivity (also called recall rate in some fields) measures the proportion of actual positives which are correctly identified as such (e.g. the percentage of sick people who are identified as having the condition); and the specificity measures the proportion of negatives which are correctly identified (e.g. the percentage of well people who are identified as not having the condition). They are closely related to the concepts of type I and type II errors. A theoretical, optimal prediction can achieve 100% sensitivity (i.e. predict all people from the sick group as sick) and 100% specificity (i.e. not predict anyone from the healthy group as sick).

The concepts are expressed mathematically as follows:

sensitivity=#true positives/#true positives+#false negatives specificity=#true negatives/#true negatives+#false positives.

By "selectively" is meant the ability to affect the activity or expression of a target molecule without affecting the activity or expression of a non-target molecule.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

A "subject" as used herein refers to an organism. In certain embodiments, the organism is an animal. In certain embodiments, the subject is a living organism. In certain embodiments, the subject is a cadaver organism. In certain preferred embodiments, the subject is a mammal, including, but not limited to, a human or non-human mammal. In certain embodiments, the subject is a domesticated mammal or a primate including a non-human primate. Examples of subjects include humans, monkeys, dogs, cats, mice, rats, cows, horses, goats, and sheep. A human subject may also be referred to as a patient.

A "subject sample" can be a sample obtained from any subject, typically a blood or serum sample, however the method contemplates the use of any body fluid or tissue from a subject. The sample may be obtained, for example, for diagnosis of a specific individual for the presence or absence of a particular disease or condition.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with diminished cardiac function is within the ability of those in the art. Subjects suffering from, and suspected of suffering from, a specific disease, condition, or syndrome are not necessarily two distinct groups.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a bar graph that depicts human umbilical vein endothelial cell (HUVEC) adhesion to immobilized peptides. FIG. 1B is a bar graph that depicts human retinal microvascular endothelial cell (HMVEC) adhesion to immobilized peptides. FIG. 1C is a bar graph that depicts HRMVEC adhesion to immobilized peptides. FIG. 1D is a bar graph that depicts human dermal fibroblast (HDF) adhesion to immobilized peptides. FIG. 1E is a bar graph that depicts reactivity of Mab XL313 to immobilized peptides. FIG. 1F is a bar graph that depicts reactivity of Mab XL166 to immobilized peptides. Data bars represent mean binding±SD from at least 3 experiments each using triplicate wells. * $P<0.05$.

FIG. 2A is a Western blot depicting analysis of control not treatment (NT) and MMP-2 proteolyzed (Prot) collagen type-I (Left panel) and collagen type-IV (Right panel) probed with anti-collagen type-I specific antibody (Left panel) or anti-collagen type-IV specific antibody (Right panel). FIG. 2B is a Western blot depicting analysis of control non-proteolyzed and MMP-2 proteolyzed collagen type-I and type-IV following 16 hour incubation and probed with Mab XL313 directed to the RGDKGE (SEQ ID NO. 1) containing collagen motif. FIG. 2C is a bar graph depicting the detection of Mab XL313 reactive RGDKGE (SEQ ID NO. 1) motif in non-proteolyzed (Nat) or MMP-2 proteolyzed (Prot) collagen by ELISA. Data bars indicate mean reactivity from triple wells±SD. * P<0.05. Experiments were completed at least 3 times with similar results. FIG. 2D is a Western blot depicting the analysis of the time dependent generation of the Mab XL313 reactive epitope of collagen type-1.

FIGS. 3A-3E are data depicting the differential roles of cryptic RGD collagen motifs on angiogenesis and inflammation in vivo. Chick chorioallantoic membranes (CAMs) were either un-stimulated or stimulated with FGF-2 in the presence or absence of cortisone acetate. FIG. 3A are images of representative examples of un-stimulated or FGF-2 stimulated CAM tissues stained with Mabs XL313 and XL166 (Green). Scale bars represent 50 μm. FIG. 3B is a bar graph depicting the quantification of FGF-2 induced angiogenesis in the absence or presence of Mabs XL313, XL166 or non-specific control antibody. Data bars represent mean number of angiogenic branching vessels ±S.E from 8-10 animals per conditions. Experiments were completed at least 3 times with similar results. FIG. 3C are images of un-stimulated or FGF-2 stimulated CAMs in the absence of cortisone acetate. Representative examples of inflammatory CAM thickening (Top panel), giemsa positive inflammatory infiltrates (Middle panel) and infiltration of macrophages (green) following staining with anti-avian specific macrophage marker KUL1 (Bottom Panel). Scale bars represent 50 μm. FIG. 3D is a bar graph depicting the quantification of relative macrophage infiltration following FGF-2 stimulation in the absence of cortisone acetate. Data bars represent mean±S.E levels of KUL expressing avian macrophages per 100× microscopic field from 5 fields per CAM and 10 CAM per condition. *P<0.05. FIG. 3E is a bar graph depicting the quantification of FGF-2 induced inflammation in the absence or presence of Mabs XL313, XL166 or non-specific control antibody. Data bars represent mean percentage inflammatory CAMs ±S.E. Experiments were completed at least 3 times with similar results. * P<0.05.

FIGS. 4A-4D are images depicting generation of XL313 cryptic RGDKGE (SEQ ID NO. 1) epitope. FIG. 4A is a Western blot of whole cell lysates (Right panel) or serum free conditioned medium (Left panel) from stromal cells probed with Mab XL313 or loading control antibodies for 13-Actin or MMP-9. FIG. 4B are images of representative examples of FGF-2 stimulated CAM tissues co-stained for expression of avian macrophages (Green) and the RGDKGE (SEQ ID NO. 1) containing epitope (Red). Scale bars indicate 50 μm. FIG. 4C is a Western blot of whole cell lysates (Right panel) or serum free conditioned medium (Left panel) from macrophage cell lines probed with Mab XL313 or loading control antibodies for β-Actin or IGFBP-4. FIG. 4D is a Western blot of whole cell lysates or serum free conditioned medium from RAW 264.7 macrophage cell that were either not transfected (WT) or transfected with α2(I) specific shRNA (Col 1 Kd) or control non-specific shRNA (Cont Kd) with Mab XL313 (Left panel) or anti-collagen-1 antibody (right).

FIG. 5A is a bar graph depicting serum from chick embryos in which the CAMs had been either not stimulated (NT) or stimulated with FGF-2 was collected. Relative levels of circulating Mab XL313 reactive epitope were quantified by solid-phase ELISA. Data represent mean Mab XL313 reactivity ±S.E (N=12 to 13). FIG. 5B is a bar graph depicting quantification of dose dependent induction of angiogenesis by RGDKGE (SEQ ID NO. 1) containing collagen peptide P-2. Data bars indicate mean number of branch points ±S.E from 8 to 12 animal per condition. FIG. 5C is a bar graph depicting quantification of CAM angiogenesis associated with RGD containing collagen peptides P-1 (KGDRGDAPG; SEQ ID NO. 2), P-2 (QGPRGDKGE; SEQ ID NO. 3) or control peptide P-C (QGPSGSPGE; SEQ ID NO. 4). Data bars indicate mean angiogenic index derived by subtracting the number of branch points from non-stimulated CAMs ±S.E from 8 to 12 animals per condition. FIG. 5D is a bar graph depicting the quantification of CAM inflammation associated with RGD containing collagen peptides P-1 (KGDRGDAPG; SEQ ID NO. 2), P-2 (QGPRGDKGE; SEQ ID NO. 3) or control peptide P-C (QGPSGSPGE (SEQ ID NO. 4)). All experiments were conducted at least 3 times with similar results. * P<0.05.

FIG. 6A is a Western blot of examples (N=3 per condition) of total lysate from un-stimulated (NT) or CAMs stimulation with P-1 (KGDRGDAPG (SEQ ID NO. 2)) or P-2 (QGPRGDKGE (SEQ ID NO. 3)) and probed for phosphorylated P38MAPK (P-p38), total P38MAPK (T-p38) or β-Actin. FIG. 6B is a bar graph depicting the quantification (Image-J) of the mean relative levels of phosphorylated P38MAPK from un-stimulated or following CAM stimulation with P-1 (KGDRGDAPG (SEQ ID NO. 2); SEQ ID NO. 2) or P-2 (QGPRGDKGE; SEQ ID NO. 3). Data bars represent mean levels of phosphorylated P38MAPK ±S.D (N=8 to 10 CAMs per condition). FIG. 6C are images of representative examples of P-2 stimulated CAM tissues co-stained for expression of vWf and phosphorylated P38MAPK. Scale bar indicates 50.0 μm. FIG. 6D is a Western blot analysis of endothelial cell (HUVEC) lysates from cells attached to collagen peptides P-1 (KGDRGDAPG; SEQ ID NO. 2), P-2 (QGPRGDKGE; SEQ ID NO. 3) and probed for phosphorylated P38MAPK (P-p38), total P38MAPK (T-p38) or β-Actin. FIG. 6E is a Western blot analysis of endothelial cell (HRMVEC) lysates from cells attached to collagen peptides P-1 (KGDRGDAPG (SEQ ID NO. 2)), P-2 (QGPRGDKGE (SEQ ID NO. 3)) and probed for phosphorylated P38MAPK (P-p38), total P38MAPK (T-p38) or β-Actin. FIG. 6F is a bar graph depicting the quantification of collagen peptide P-2 (QGPRGDKGE (SEQ ID NO. 3)) induced angiogenesis in the chick CAM following treatment with P38MAPK inhibitor (P38IN) of DMSO control (Cont). Data bars represent angiogenic vessel branch points ±S.E (N=8-12 per condition). Experiments were conducted at least 3 times with similar results. * P<0.05.

FIGS. 7A and 7B are bar graphs depicting that endothelial cells (HUVECS) were allowed to bind to wells coated with either RGDKGE (SEQ ID NO. 1) containing collagen peptide P-2 (FIG. 7A) or RGDAPG (SEQ ID NO. 11) containing collagen peptide P-1 (FIG. 7B) in the presence or absence of function blocking anti-integrin antibodies. Data bars represent mean cell adhesion (±S.E. from 4 experiments). *p<0.05. FIG. 7C is a Western blot of HUVEC lysates following binding to RGD containing collagen peptides P-1 or P-2 probed with anti-phosphorylated β3-integrin (p-β3), total β3-integrin (T-β3) or β-Actin. FIG. 7D is a Western blot of HUVEC lysates following binding to RGD containing collagen peptides P-1 or P-2 probed with anti-phosphorylated Src (P-Src), total Src (T-Src) or β-Actin. FIG. 4E is a Western blot of lysates prepared from HUVECs incubated in the presence or absence of a Src inhibitor PP2 (Src-IN) or control DMSO (cont) following binding to RGD containing collagen peptides P-1 or P-2 probed with anti-phosphorylated β 3-integrin (p-β 3), total β 3-integrin (T-β 3) or β-Actin. FIG. 7F is a Western blot of lysates prepared from HUVECs incubated in the presence or absence of a Src inhibitor PP2 (Src-IN) or control DMSO (cont) following binding to RGD containing collagen peptides P-1 or P-2 probed with anti-phosphorylated P38MAPK (p-P38), total P38MAPK- (T-P38) or β-Actin. FIG. 7G are images of representative examples of endothelial cells (HUVECs) attached to RGD containing collagen peptides P-1 and P-2 stained for F-actin. Scale bar indicates 50.0 μm.

FIG. 8A are images of representative examples of endothelial cells (HUVECs) attached to RGD containing collagen peptides P-1 and P-2 stained for YAP (green). Scale bar indicates 50.0 μm. FIG. 8B is a Western blot of cytoplasmic (left) and nuclear (right) fractions of HUVEC lysates following binding to RGD containing collagen peptides P-1 or P-2 probed with anti-YAP, β-tubulin and anti-total binding protein (TBP). FIGS. 8C and 8D are bar graphs depicting the quantification of HUVEC (FIG. 8C) and HRMVEC (FIG. 8D) growth in the presence or absence of exogenously added RGD containing peptides P-1 or P-2. Data bars represent mean endothelial cell growth (±S.E) from 3 to 4 independent experiments expressed as percent of control. FIG. 8E is a Western blot of isolated nuclear fractions from cell lysates of endothelial cells (HRMVEC) following stimulation with soluble RGD containing collagen peptides P-1 or P2 and probed with YAP or total binding protein (TBP). FIG. 8F is a Western blot of isolated nuclear fractions from cell lysates of endothelial cells (HRMVEC) pre-incubated with Src or P38MAPK inhibitor and stimulation with soluble RGD containing collagen peptides P-1 or P-2 and probed with YAP or total binding protein (TBP). FIGS. 8G and 8H are bar graphs depicting the quantification of endothelial cell growth in the presence or absence of exogenously added RGD containing peptides P-1 or P-2 from cells transduced with non-specific shRNA (FIG. 8G) or YAP specific shRNA (FIG. 8H). Data bars represent mean endothelial cell growth (±S.E) from 4 independent experiments. FIG. 8I is a bar graph depicting the quantification of endothelial cell growth in the presence or absence of exogenously added VEGF (50 ng/ml) or 10% serum from cells transduced with YAP specific shRNA. Data bars represent mean endothelial cell growth (±S.E) from 4 independent experiments. * P<0.05.

FIGS. 14A and 14B are blots of integrin αvβ3 expressing melanoma cells (M21 and CLL-49) and FIG. 14C is a blot depicting that endothelial cells (HUVEC) were allowed to attach to well coated with either a non-αvβ3 binding ligand (native collagen-IV) or an αvβ3 binding ligand (denatured collagen-IV). Whole cell lysates were prepared and the relative levels of PDL-1 or loading control β-actin were assessed by Western blot.

DETAILED DESCRIPTION OF THE INVENTION

Figure 1A:
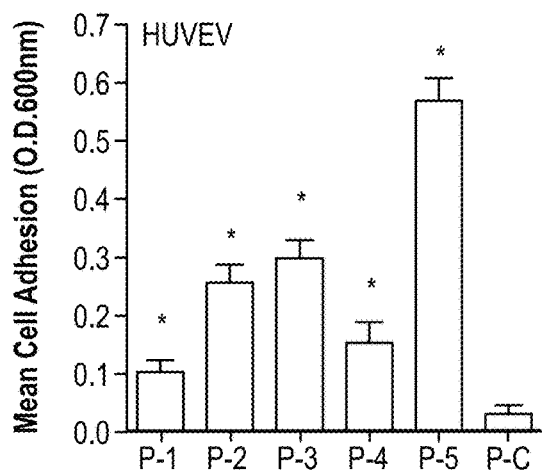
FIGS. 1A-1F are bar graphs of cryptic RGD containing peptides from collagen type-I support cell adhesion. Peptides corresponding to the 5 different RGD-containing motifs of human collagen type-I were synthesized with flanking cysteines and immobilized non-tissue culture plates. The ability of stromal cells to attach (FIGS. 1A-1D) or monoclonal antibodies to bind the immobilized peptides (FIGS. 1E-1F) was assessed.

Described herein is an RGD containing cryptic collagen epitope that is generated in vivo. As described in detail below, rather than inhibiting αvβ3 signaling, this collagen epitope promoted αvβ3 activation and stimulated angiogenesis and inflammation. Additionally, an antagonist of integrin αvβ3 that inhibits signaling from this receptor was used to enhance the therapeutic activity of PD-1/PDL-1 targeting drugs for the treatment of cancer and other diseases characterized by abnormal immune response.

Also described herein is an endothelial cell mechano-signaling pathway in which a cryptic collagen epitope activates αvβ3 leading to a Src and P38MAPK-dependent cascade that leads to nuclear accumulation of YAP and stimulation of endothelial cell growth is defined. Collectively, the findings provide evidence for a mechano-signaling pathway, but also define a potential therapeutic strategy to control αvβ3 signaling by targeting a pro-angiogenic and inflammatory ligand of αvβ3 rather than the receptor itself.

Angiogenesis, the process by which new blood vessels form from pre-existing vessels plays a critical role in normal and pathological events. Efforts are underway to more precisely define the interconnected mechanisms that control this crucial biological process in order to develop more effective strategies to control neovascular diseases (1, 2). Significant advances have been made in identifying molecular regulators of angiogenesis and their associated signaling pathways (3-5). A more precise understanding of angiogenic signaling pathways and the networks of regulatory feedback loops operating within distinct cellular compartments has provided important clues to help explain the modest clinical impact of many anti-angiogenic strategies (1-5). For example, while vascular endothelial growth factor (VEGF) induces pro-angiogenic signaling leading to enhanced endothelial cell migration, growth, and survival, VEGF-induced blood vessels are often characterized as immature, unstable, and leaky and can regress in the absence of additional signaling events (6). VEGF stimulation under specific circumstances may lead to inhibition of angiogenesis in the context of altered PDGF signaling do to disruption of pericyte recruitment (6). These unexpected findings provide evidence of a negative role for the VEGF/VEGFR signaling during new vessel development (6). Similarly, studies have provided evidence for both a positive and a negative role for integrin αvβ3 in angiogenesis (7-9).

A wide array of alterations in the composition and bio-mechanical properties of extracellular matrix (ECM) proteins are known to occur during angiogenesis and studies are beginning to define how these changes contribute to new blood vessel development (18,21-23,51-53). Among the key cell surface molecules that play roles in mechano-transduction to facilitate information flow from outside the cell to the inside are integrin receptors. Integrins may act like information hubs by sensing diverse extracellular inputs and relaying this information into a complex network of intracellular circuits that ultimately modulate cellular behavior (4). The precise molecular mechanisms by which cells fine-tune their response to changes within the stromal microenvironment are not completely understood. Further complicating the understanding of new vessel development is the expanding number of cell types that contribute to tissue specific control of angiogenesis such as distinct subsets of stromal fibroblasts, progenitor cells and a variety of inflammatory cells such as neutrophils, mast cells and macrophages. The roles played by these diverse cells during angiogenesis range from secretion of cytokines, chemokines and proteolytic enzymes to the differential expression of other pro and anti-angiogenic factors. Thus, tight control mechanisms must operate to allow coordination between these diverse compartments to govern tissue specific vascular responses.

Integrins are molecules with the ability to detect compositional and structural changes within the ECM and integrate this information into a network of signaling circuits that coordinate context dependent cell behavior. Among the most well studied integrins known to play a role in angiogenesis is αvβ3. The complexity by which αvβ3 regulates angiogenesis is illustrated by the fact that this receptor may exhibit both pro and anti-angiogenic functions (7-15). It is indicated that the distinct biological responses stimulated by binding to αvβ3 may depend on many factors including the mechanical and biochemical features of the particular ligands, the cell types within which αvβ3 is expressed as well as the concentration and manner by which the ligands are presented to the receptor (7-9,24-27). For example, studies indicate that αvβ3 binding to specific NC1 domains of collagen or selected RGD peptides can induce apoptosis, induce arteriole contraction and inhibit angiogenesis (19,29, 54) while other αvβ3 ligands may promote cell survival, induce vascular dilation and support angiogenesis (21-23, 30,55). These observations are consistent with the notion that the final outcome of αvβ3-mediated signaling may depend to a large extent on the particular characteristics of the ligand. While a wealth of data has shown that RGD peptides can inhibit angiogenesis when administered exogenously, the approach of using a cyclic RGD peptide to control tumor growth failed to significantly impact glioblastoma progression and patient survival in late stage clinical testing (31). Interestingly, studies have indicated that specific RGD peptides may active β3 integrins (56, 57) and under defined experimental conditions induce angiogenesis and tumor growth (30). These findings and other studies suggesting that amino acids C-terminal to the RGD motif play roles in governing integrin selective binding, prompted the examination of the biological significance of naturally occurring RGD containing epitopes on angiogenesis.

For example, multiple pro-angiogenic roles have been proposed for αvβ3 as cyclic arginine-glycineaspartic acid (RGD) containing peptides and antibodies targeting this integrin inhibit angiogenesis in animal models (10-12). In contrast, enhanced angiogenesis was detected in tumors growing in αvβ3 null mice (13). Interestingly, reduced pathological angiogenesis was detected in transgenic mice expressing signaling deficient β3 integrin, which resulted in part from defective recruitment of bone marrow derived cells rather than specific endothelial cell defects (14). Moreover, evidence suggests that β3 integrin may play a more prominent role in the early stages of angiogenesis when new vessels begin to form, as reduction in endothelial cell expression of β3 integrin impaired early stage pathological angiogenesis, but had little effect on later maturation stages once vessels had formed (15). These studies, together with many others suggests αvβ3-mediated regulation of angiogenesis is complex, temporally regulated and is not solely dependent on adhesive events, but also involves downstream signaling, the consequences of which may depend on the cell type and composition of the local extracellular microenvironment (4,9,12,16). Because of the opposing biological responses observed following modulation of some angiogenic regulatory molecules, it is not surprising that anti-angiogenic strategies based on targeting these factors have met with limited clinical success.

Given the importance of integrin-extracellular matrix (ECM) interactions in modulating the intensity and specificity of growth factor signaling (1-5, 17, 18), it is important to define how diverse components within the local vascular microenvironment function cooperatively to regulate angiogenesis. Interestingly, distinct αvβ3 ligands may stimulate opposing biological outcomes (7-15). For example, certain NC1 domains of collagen may bind αvβ3 and induce proapoptotic responses while binding of other αvβ3 ligands may promote cell growth and survival (19-22). Given these findings and the complex biological effects observed following direct targeting of αvβ3, an alternative therapeutic approach to control signaling from αvβ3 might involve specific targeting of the pro-angiogenic ligands of αvβ3 rather than directly targeting the receptor itself. Proteolytic remodeling of the ECM can generate integrin binding cryptic epitopes that play functional roles in angiogenesis including the LPGxPG containing HU177 cryptic epitope present in multiple types of collagen and the HUIV26 cryptic epitope, which is present in collagen type-IV (21-23). While the HUIV26 epitope is recognized by αvβ3, it is not specifically composed of an RGD motif (21).

Sequence analysis of RGD sites within collagen type-I indicate that the KGE tri-peptide motif that is C-terminal to the RGD site was highly conserved among diverse species, while considerable variation is observed in the other collagen RGD flanking sequences. While all five of the collagen RGD epitopes can support cell binding, the highly conserved RGDKGE (SEQ ID NO. 1) collagen peptide P-2 may play a functional role angiogenesis and inflammation given that Mab XL313 directed to this epitope but not an antibody that recognizes the other three RGD collagen sites inhibited angiogenesis and inflammation in vivo. While the precise difference between the three other naturally occurring non-RGDKGE (SEQ ID NO. 1) containing collagen epitopes, one or more of these epitopes were detected in vivo in addition to the RGDKGE (SEQ ID NO. 1) epitope. Given that these RGD containing epitopes are thought to be largely cryptic and not readily accessible to cell surface receptor, the findings are consistent with active collagen remodeling resulting in generation neoepitopes during new vessel formation.

Because of the importance of RGD sequences in mediating some integrin-dependent interactions and the roles of amino acids flanking the core RGD motif in establishing integrin-binding specificity and affinity (24-27), the ability of RGD motifs within collagen differentially regulate angiogenesis was determined. Sequence analysis of collagen type-I revealed that five different cryptic RGD motifs are present, each with unique flanking sequences. Surprisingly, the C-terminal KGE flanking sequence of one of these RGD motifs is highly conserved in species as diverse as xenopous and man. In contrast, significant sequence and positional variation exists within the other flanking sequences among different species.

ECM remodeling occurs as an early event during angiogenesis and multiple proteolytic enzymes including matrix metalloproteinase (MMPs) as well as serine and cysteine proteases the have the capacity to degrade intact or structurally altered forms of collagen (18,58). While the in vitro studies indicate that MMP-2-mediated degradation of collagen can lead to the generation of low molecular weights fragments recognized by Mab XL313, the precise mechanism by which the RGDKGE (SEQ ID NO. 1) collagen epitope is generated in vivo is not completely understood. Analysis of angiogenic CAM tissues suggests that a subset of macrophages may be an important source of the RGDKGE (SEQ ID NO. 1) epitope. Activated macrophages with M2-like characteristics can express multiple enzymes capable of degrading collagen and in turn can internalize and further degrade collagen into small low molecular weight fragments (35,38). While little evidence exist that macrophages generate and deposit intact triple helical collagen type-I, studies have indicated that certain isoforms of collagen may be expressed (59). Consistent with previous reports, intact collagen was detected; however low molecular weight RGDKGE (SEQ ID NO. 1) containing collagen fragments in both whole cell lysates and serum free conditioned medium from macrophages like cell lines was detected. While the studies do not rule out macrophage mediated collagen internalization as a contributing factor to the in vivo generation the RGDKGE (SEQ ID NO. 1) collagen epitope, the in vitro studies were carried out in the absence of serum or exogenously added collagen, and thus are consistent the active generation of the RGDKGE (SEQ ID NO. 1) collagen fragment by macrophages.

Activated macrophages including M2-polarized macrophages have been implicated in supporting angiogenesis and inflammation as multiple factors secreted by these cells exhibit pro-angiogenic activities (35,60). While many studies indicate that synthetic RGD containing peptides inhibit angiogenesis and tumor growth, the findings provide the first evidence that macrophages may generate and release an RGDKGE (SEQ ID NO. 1) containing collagen epitope that may exhibit pro-angiogenic activity. Importantly, previous studies have suggested that certain RGD-peptides can activate αvβ3 (56,57) and may enhance vascular permeability (45,55), which might lead to release of inflammatory factors, which may in turn contribute to the formation of new blood vessels.

To examine possible mechanisms by which the RGDKGE (SEQ ID NO. 1) collagen peptide might regulate angiogenesis endothelial cell receptors for this motif were identified. While the possibility that additional non-integrin receptors may bind this collagen epitope is not ruled out, the data suggest that αvβ3 can function as an endothelial cell receptor for the RGDKGE (SEQ ID NO. 1) motif. Interestingly, αvβ3 bound both the RGDKGE (SEQ ID NO. 1) and RGDAPG (SEQ ID NO. 11) collagen peptides, yet only RGDKGE (SEQ ID NO. 1) peptide significantly induced angiogenesis and inflammation in vivo. These findings are consistent with the notion that distinct RGD containing αvβ3 ligands may promote different biological responses. Signaling downstream from αvβ3 is complex and studies have indicated that simple binding of β3 integrin does not necessarily lead to productive outside-in integrin signaling (61). In fact, the capacity of β3 integrins to promote outside-in signaling depends on multiple factors including the extent of receptor clustering and subsequent generation of mechanical tension within the actin cytoskeleton, recruitment of adaptor and accessory proteins such as Ga13, and Kindlin-2 and the association of the integrin with protein tyrosine phosphatases and certain growth factor receptors (62-65). While the exact mechanisms leading to RGDKGE (SEQ ID NO. 1)-mediated αvβ3 signaling is not completely understood, endothelial cell interactions with the RGDKGE (SEQ ID NO. 1) peptide in the absence of serum led to enhanced phosphorylation of β3 integrin on tyrosine 747 and of Src phosphorylation at tyrosine 416. These data and others are consistent with an early mechanical mediated activation of β3 integrin that depends on Src given that blocking Src activity reduced β3 phosphorylation following binding to the RGDKGE (SEQ ID NO. 1) motif.

Integrin signaling and Src activation are known to regulate the architecture of the actin cytoskeleton (66). Moreover, Src family kinases regulate P38MAPK, and activation of P38MAPK is thought to enhance actin stress fiber formation in endothelial cells and regulate angiogenesis in vivo (39-45). The findings provide insight into the coordinated roles of P38MAPK and Src in regulating RGD-dependent endothelial cell signaling through αvβ3 as interactions with the RGDKGE (SEQ ID NO. 1) cryptic collagen epitope leads to enhanced P38MAPK phosphorylation in a Src-dependent manner. Moreover, RGDKGE (SEQ ID NO. 1)-induced angiogenesis in vivo was associated with enhanced levels of phosphorylated P38MAPK, and this angiogenic response was reduced by an inhibitor of P38MAPK. These findings are consistent with the notion that RGDKGE (SEQ ID NO. 1) stimulated angiogenesis depends on P38MAPK.

Recent studies have suggested a role for actin stress fibers and mechanical tension in promoting nuclear accumulation of YAP, where it is thought to function in conjunction TEAD transcription factors in regulating gene expression (46-50). Given data suggesting a role for YAP in regulating endothelial cell growth and angiogenesis, the subcellular distribution of YAP in endothelial cells following interaction with the RGDKGE (SEQ ID NO. 1) collagen peptide was examined. The data indicate that endothelial cell interaction with the RGDKGE (SEQ ID NO. 1) epitope was associated with enhanced nuclear accumulation of YAP. Integrin signaling may play a role in the regulation of YAP as studies have implicated a role for β1 integrins expressed in skeletal stem cells and αv integrins expressed in osteoblasts in governing YAP subcellular localization (67,68). The findings are consistent with a mechanism by which αvβ3-mediated binding to the RGDKGE (SEQ ID NO. 1) epitope, but not the related RGDAPG (SEQ ID NO. 11) epitope stimulates a signaling cascade leading to enhanced nuclear accumulation of YAP that depends on Src and/or P38MAPK. This possibility is supported by the findings that reduced levels of nuclear YAP was detected following αvβ3-mediated interaction with RGDKGE (SEQ ID NO. 1) peptide in endothelial cells in which Src or P38MAPK was inhibited. Given the documented role of YAP in governing cell growth coupled with the ability of the RGDKGE (SEQ ID NO. 1) collagen peptide to stimulate nuclear accumulation of YAP and enhance endothelial cell growth, it is possible that the RGDKGE (SEQ ID NO. 1) collagen peptide-induced endothelial cell growth is YAP dependent. Consistent with this possibility, no enhancement of endothelial cell growth was detected following knockdown of YAP in endothelial cells stimulated with the RGDKGE (SEQ ID NO. 1) collagen peptide, even though these cells are capable of proliferating as stimulation with VEGF or high levels of serum enhanced their growth. Given the studies, it is possible that part of the FGF-2 induced angiogenic response observed in the chick CAM model might involve the recruitment of macrophages that generate a previously uncharacterized RGDKGE (SEQ ID NO. 1) containing cryptic collagen epitope that binds to αvβ3 leading to Src and P38MAPK activation and nuclear accumulation of YAP. Given that YAP is known to regulate a wide array of genes that may impact angiogenesis and inflammation including CTGF and Cry61, it is likely that the RGDKGE (SEQ ID NO. 1) collagen epitope may initiate a complex pro-angiogenic program in vivo involving YAP-associated regulation of multiple pro-angiogenic molecules and not simply be restricted to only enhancing endothelial cell growth.

Collectively, the results presented herein provide evidence that a highly conserved RGDKGE (SEQ ID NO. 1) containing collagen epitope can be generated by a subset of macrophages and the RGDKGE (SEQ ID NO. 1) collagen epitope can stimulate pro-inflammatory and angiogenic activity. Binding of the RGDKGE (SEQ ID NO. 1) collagen epitope to β3 integrin can initiate a signaling pathway in endothelial cells leading to activation of Src and P38MAPK ultimately leading to nuclear accumulation of YAP and enhance cell growth. The results presented herein provide cellular and molecular insight into how an endogenously generated RGD containing cryptic collagen epitope may promote rather that inhibit angiogenesis. Given the complexity of αvβ3 functions and the growing body of evidence that the final outcome of αvβ3 binding may depend on the nature of the particular ligand, the findings provide support for an alternative strategy to help control the biological activity of β3 integrin by specific targeting of endogenous pro-angiogenic ligands of αvβ3 rather than direct targeting of the receptor itself.

Integrin αvβ3 plays a functional role in promoting immune suppression in part by upregulating the expression of the immune checkpoint regulatory protein PDL-1. Thus, targeting αvβ3 with function blocking (signal blocking) antagonists of αvβ3 or reducing expression of αvβ3 led to reduced expression of PDL-1. Thus antagonist of αvβ3 may enhance the anti-tumor efficacy of immune checkpoint therapy. Importantly, while immune check point inhibitors are known to provide some anti-tumor activity in humans, this partial anti-tumor activity is only observed in a fraction of treated subjects. Described herein is the identification of compounds and combination treatment strategies to enhance the efficacy of immune checkpoint inhibitors such as CTLA-4, PDL-1 and PD-1 antibodies.

Therapeutic blockade of immune checkpoint regulatory molecules such as CTLA-4 and PD-1/PDL-1 signaling is known to be associated with significant immune related side effects including inflammation. Given these known side effects of immune checkpoint therapy and the ability of specific ligands of αvβ3 integrin such as the RGDKGE (SEQ ID NO. 1) containing collagen epitope to potentially induce inflammation in vivo, combining antagonist of αvβ3 with anti-PD-1/PDL-1 antagonists may reduce the inflammatory side effects associated with immune checkpoint inhibitor therapy.

Herein, is in vivo animal data, which indicate that melanoma tumors that express integrin αvβ3 express the immune checkpoint protein PDL-1, while the same tumor cell type that was selected for lack of functional αvβ3 exhibited little detectable PDL-1. Second, cellular interactions of tumor cells as well as endothelial cells with ECM proteins (denatured collagen and the RGDKGE (SEQ ID NO. 1) collagen epitope) that documented ligands of integrin αvβ3 lead to upregulated expression of PDL-1. Third, a function blocking antibody directed specifically to integrin αvβ3 reduced expression of PDL-1 in tumor cells. Finally, an antibody (Mab XL313) that specifically blocks the binding of an RGDKGE (SEQ ID NO. 1) epitope to αvβ3 and inhibits downstream signaling from αvβ3 enhanced the anti-tumor efficacy of an immune checkpoint inhibitor (anti-PDL-1) in vivo.

Previous studies have indicated that blockade of immune checkpoint proteins such as PDL-1 can result in some anti-tumor activity. These anti-tumor effects, however were only partial and only occurred in a fraction of the treated subjects. Thus, described herein is the identification of compounds that enhance the effect of immune checkpoint inhibitors such as antibodies targeting CTLA-4, PD-1 and/or PDL-1. To this end, studies have suggested that combining immune checkpoint inhibitors with other chemotherapy drugs may enhance the anti-tumor activity. Importantly, a common side effect that can limit the use of immune checkpoint inhibitors is the active induction of inflammatory conditions such as dermatitis, pneumonitis and colitis. In this regard, antagonists of the XL313 epitope (Mab XL313) no only enhance the therapeutic activity of an anti-PDL-1 antibody therapy in a mouse model (FIG. 9), but Mab XL313 epitope potently inhibits inflammation in vivo. Additionally a αvβ3 binding RGDKGE (SEQ ID NO. 1) containing collagen epitope that stimulates αvβ3 integrin signaling was shown to significantly enhance inflammation in vivo. Given these findings, it is possible that blocking αvβ3 signaling with an antagonist of αvβ3 would not only enhance the therapeutic activity of an anti-PDL-1/PD-1 or CTLA-4 based therapy, but may also potently inhibit inflammation in vivo. These findings are consistent with the notion that combining an antagonist of XL313 epitope (or antagonist of αvβ3) with immune checkpoint inhibitor therapy not only enhances its efficacy, but also reduces the inflammatory side effects observed with the immune checkpoint inhibitor therapy.

Described herein is evidence that an RGDKGE (SEQ ID NO. 1) containing cryptic collagen epitope is generated by a subset of macrophages and this motif promoted rather than inhibited angiogenesis. These findings are surprising given the wealth of experimental data indicating the high concentration of RGD peptides inhibit rather than induce angiogenesis (11, 28, 29). Increasing evidence suggests that low concentrations of certain RGD peptides may actually enhance angiogenesis and tumor growth (30), which may explain at least in part the minimal impact of cyclic RGD peptide antagonists of αvβ3 and αvβ5 in human clinical trials (31). In addition to variations in concentrations that alter the biological response of certain RGD peptides, the specific composition of the amino acids C-terminal to RGD motif within naturally occurring epitopes may confer unique pro-angiogenic and inflammatory activity. Taken together, these results are consistent with a mechanism by which the RGDKGE (SEQ ID NO. 1) collagen epitopes induce angiogenesis and inflammation by stimulating mechanical activation of αvβ3 leading to Src-dependent phosphorylation of P38MAPKinase that promotes nuclear accumulation of the Yes-associated protein (YAP) and enhanced endothelial cell growth.

EXAMPLES

Example 1

Materials and Methods

Reagents, Kits, Chemicals and Antibodies

Ethanol, methanol, acetone, bovine serum albumin (BSA), crystal violet, phosphate-buffered saline (PBS), purified human collagen type-IV and collagen type-I, AMPA, 3,3,5,5' tetramethybenzidine (TMB), phosphatase inhibitor cocktail, and cortisone acetate (CA) were from Sigma (St Louis, Mo.). MMP2 was from Chemicon/Millipore (Billerica, Mass.). FBS was from Science Cell (Carlsbad, Calif.). Fibroblast growth factor-2 (FGF-2) was obtained from R&D Systems (Minneapolis, Minn.). Nuclear/Cytoplasmic fractionation kit was from Thermo Scientific (Waltham, Mass.). P38MAPK inhibitor, SB202190 was obtained from CalBoichem (San Diego, Calif.). RIPA buffer, protease inhibitor, and Src inhibitor (PP2) were from Santa Cruz (Santa Cruz, Calif.). Anti-vWf antibody was from BD Pharmingen (San Diego, Calif.). Antibodies directed to P38MAPK, phospho-P38MAPK (Thr-180/Tyr-182), Src, and phospho-Src (Tyr 416), were from Cell Signaling Technology (Danvers, Mass.). Antibodies against tubulin, total binding protein (TBP), YAP, β3, and phospho-133 (Tyr747) were from Santa Cruz (Santa Cruz, Calif.). Anti-Igfbp4 and anti-MMP9 antibodies were obtained from Abcam (Cambridge, Mass.). Function blocking antibodies P4C10 (anti-β1), LM609 (anti-αv β3) and P1F6 (anti-αv β5) were from R&D Systems (Minneapolis, Minn.). HRP-conjugated secondary antibodies were from Promega (Madison, Wis.). Anti-collagen type-I antibody was from Rockland (Limerick, Pa.) and anti-collagen type-IV was from Millipore (Billerica, Mass.). Mouse monoclonal antibodies XL313, and XL166 were developed. Alexa-488, Alexa-594, streptavidin Alexa-594, and phalloidin Alexa-594 labeled antibodies were from Invitrogen (Carlsbad, Calif.). Synthetic collagen RGD containing peptides (P-1; CKGDRGDAPGC (SEQ ID NO. 5), P-2; CQGPRGDKGEC (SEQ ID NO. 6), P-3; CAGSRGDGGPC (SEQ ID NO. 7), P-4; CQGIRGDKGE (SEQ ID NO. 8), P-5; CRGPRGDQGPC (SEQ ID NO. 9) and peptide control (P-C; CQGPSGAPGEC; SEQ ID NO. 10) were obtained from QED Biosciences (San Diego, Calif.).

Cells and Cell Culture

RAW 264.7 and THP-1 cells were from ATCC (Manassas, Va.) and cultured in DMEM and RPMI respectively in the presence of 10% FBS, 1.0% pen-strep and 1.0% sodium pyruvate. Immortalized BV-2 cells, and were cultured in DMEM with 10% FBS, 1.0% pen-strep and 1.0% sodium pyruvate. Human dermal fibroblasts (HDF) were obtained from Science Cell (Carlsbad, Calif.) and cultured in fibroblast growth medium with 2.0% FBS and used between passages 4 to 9. Human retinal microvascular endothelial cells (HRMVECs) were obtained from Applied Cell Biology Institute (Kirkland, Wash.) and cultured in EBM2 supplemented with EGM-2 growth factors. Human umbilical vein endothelial cells (HUVECS), human microvascular endothelial cells (HMVECS) were obtained from ATCC (Manassas, Va.) and cultured in EBM2 with supplemental growth factors EGM-2 or EGM-2MV respectively. All endothelial cell growth media contained 2% FBS, 1.0% pen-strep and 1.0% sodium pyruvate and used experimentally between passages 3 to 9. For collection of conditioned media, cells were cultured in basal media under serum free conditions for 24 hours. Conditioned media was collected and concentrated 10× using an Amicon Ultracell, 3 kDa centrifugal ultrafiltration cartridge.

Cell Adhesion Assays

RGD peptides (P-1, P-2, P-3, P-4, P-5, and P-C) were immobilized (100 μg/ml) to wells. HUVEC, HMVEC, HRMVEC, and HDF cells were suspended in adhesion buffer (RPMI containing 1 mM $MgCl2$, 0.2 mM $MnCl2$ and 0.5% BSA) and 1×105 cells were seeded into the wells in the presence or absence of P4C10, LM609, P1F6 or control antibodies (100 μg/ml). Cells were allowed to attach for 25 min at 37° C. Media containing non-attached cells was aspirated and attached cells were washed with PBS and stained with crystal violet. Cell adhesion was quantified by measuring the optical density of eluted dye. Adhesion assays were completed at least three times with triplicate wells.

Collagen Proteolysis and Solid Phase Binding Assays

Collagen type-I and collagen type-IV were heat denatured for 15 min and then incubated with APMA-activated MMP2 for 0.5 h, 1 h, 4 h, 8 h, and 20 h, at 37° C., followed by a five minute boil to deactivate remaining MMP. For solid phase ELISAs, synthetic RGD-containing collagen peptides (P-1, P-2, P-3, P-4, P-5, and P-C) were immobilized (100 μg/ml) to wells or wells were, coated with 10 μg/ml of native or MMP2-proteolyzed collagen type-I or type-IV. Wells were blocked with 1% BSA in PBS for 1 hour and then incubated with 1 μg/ml of Mabs XL313 or XL166 for 1 h, washed, and incubated with antimouse HRP-conjugated antibodies (1:5000). Bound Mabs were detected with a TMB substrate as per manufactures instructions and quantified via spectrometer measurements. All assays were carried out at least four times in triplicate wells.

Chick Cam Inflammation and Angiogenesis Assays

The chick chorioallantoic membrane (CAM) assays were carried out with some modifications (19). For all experiments CAMs of 10-day-old chick embryos obtained from Charles River (North Franklin, Conn.) were separated from the shell membrane. Filter discs either non-treated (inflammation assays) pretreated (angiogenesis assays) with cortisone acetate (3.0 mg/ml) containing RPMI only or FGF-2 (40 ng). CAMs were either non-treated or treated topically with Mab XL313, XL166 or a non-specific control antibody (10 μg/embryo every 24 h for three consecutive treatments). For peptide induction experiments, CAMs were stimulated with 100 ng/ml of the RGD peptides (P-1, P-2, P-C) in the presence or absence of the P38MAPK inhibitor, SB202190 (10 μM). At the end of the incubation period the embryos were sacrificed and the CAM tissues were analyzed. Angiogenesis was quantified by counting the number of angiogenic branching blood vessels within the area of the filter disc. The angiogenic index was determined by subtracting the mean number of blood vessel branch points from untreated CAMs from each experimental condition. Eight to twelve embryos were used per condition and experiments were repeated at least three times.

Immunohistochemistry and Immunofluorescence Analysis

CAMs examined for accumulation of granulation tissue were harvested, fixed in 4% PFA and paraffin embedded and sectioned (4 μm) and stained with Giemsa. CAM tissues analyzed via immunofluorescence were harvested, embedded with OCT, snap frozen and sectioned (4 μM). Frozen sections were fixed in 50% methanol/50% acetone, air dried and blocked with 2.5% BSA for 1 h at 37° C. For expression of the XL313 and XL166 epitopes as well as monocyte/macrophages, FGF-2 stimulated CAM tissues were stained with Mabs XL313, XL166 (50 μg/ml) or KUL1 (1:250) and then incubated with Alexa-488 labeled secondary antibodies (1:2000 dilution). Co-staining of monocytes/macrophages and the Mab XL313 reactive epitope in FGF-2 stimulated CAMs was performed by sequential staining by first probing with KUL1 (1:250) and then with a biotinconjugated Mab XL313 (50 μg/ml), and with secondary antibodies Alexa-488 and streptavidin Alexa-594 (1:2000) respectively. Using a similar strategy, sections of RGD peptide-treated CAM tissues were analyzed for phosphorylated-P38MAPK in angiogenic vessels by co-incubation of anti-phospho-P38MAPK (1:50) and anti-vWf (1:500) antibodies. Subcellular localization of YAP was observed in HUVECS attached to P-2 and P-1 coated glass coverslips. Cells were allowed to attach for 15, 30, or 60 min in the absence of serum and were fixed with 4% PFA. Fixed cells were washed and blocked with 2.5% BSA and stained with anti-YAP (1:200) and phalloidin (1:500). All sections and slides were counter stained with DAPI.

Cell Proliferation Assays

HUVECs (WT, shYAP1 or control transfected) or HRMVECs were plated at 2,000 cells per well with complete EGM-2 media containing 2.0% FBS in the absence or presence of P-1, P-2 or P-C (100 ng/ml) and allowed to grow for 24 hours. Cell growth was monitored using a BrdU or MMT assay kits according to manufacturer's instructions. All assays were completed at least three times in triplicate wells.

Inhibitor Experiments

Endothelial cells (HUVECs or HRMVECs) were incubated in serum free media with 1 mM $MgCl_2$, 0.2 mM $MnCl_2$ in the presence of a Src inhibitor, PP2, (10 μM) a P38MAPK inhibitor, SB202190 (10 μM) or vehicle only (DMSO) for 10 min at 37° C. Treated cells were then seeded on to immobilized P-1 and P-2 and lysates were collected at 15 min.

Western Blots

Whole cell and CAM tissue lysates were collected in RIPA buffer supplemented with 1× protease inhibitor and 1× phosphatase inhibitor and were run on polyacrylamide gels using denaturing conditions. Prior to loading the gels, 6× sample buffer was added to each of the lysates (final concentration 1×) and boiled for five minutes. Twenty to 50 μg of total protein were loaded into each lane. For detection of proteins larger than 50 kD, 10% gels were used; for proteins smaller than 50 kD 15% gels were used. Gels were run at 60 volts (v) until the dye front passed through the stacking gel, and then the voltage was increased to 100V for the remainder of the separation. Precision Plus protein standards (Bio-Rad) were used to visualize migration. Protein was transferred to nitrocellulose membranes using a wet tank system and blocked for 1 h using 10% non-fat dried milk in tris-buffered saline with 0.01% Tween-20 (TBS-T). Membranes were incubated with primary antibodies (anti-coll-I (1:250), anti-coll-IV (1:250), Mab XL313 (2 μg/ml), Mab XL166 (2 μg/ml) anti-β-actin (1:5000), anti-phospho-β3 (1:7000), anti-β3 (1:1000), anti-phospho-Src (1:500), anti-Src (1:500), anti-phospho-P38MAPK (1:500), anti P38MAPK (1:2000), anti-YAP (1:500), anti-Tubulin (1:2000), anti-TBP (1:1000)) in 5% BSA in TBS-T overnight at 4° C. with gentle agitation. Membranes were washed 3 times in TBS-T for five minutes. Blots were then incubated with HRP conjugated secondary antibodies (1:15000) in 1% non-fat milk in TBS-T for 1 h. Membranes were washed a second time as indicated above and exposed to chemiluminecent substrate for three minutes prior to exposure to autoradiography film in a dark room. Western blot bands were quantified using Image J software based on pixel intensity.

Transfections and Lentiviral Transductions

Raw cells were transfected with 1 μg of HuSH shRNA plasmids for collagen type I, alpha 2 using Amaxa cell line nucleofector kit V (program #T024). Constructs expressing 21-nucleotide short hairpin RNAs (shRNA) targeting human YAP (shYAP) or non-targeting control (shNT, Sigma-Aldrich, SHC002) were used. Humantargeting shYAP1 lentiviral shRNA was obtained from the Thermo Scientific RNAi consortium (TRCN0000107625). Constructs were packaged into lentivirus, pseudotyped with the vesicular stomatitis virus glycoprotein. Transduction was performed by incubating cells with lentivirus, and stably transduced cells were subsequently used for studies. All cell lines were verified by morphology and mouse and human YAP-specific PCR. The efficacy of YAP knock down was determined to be between 70%-80%. Endothelial cells were certified mycoplasma-negative by PCR (Lonza), and primary cell cultures were used within the indicated passage numbers. Cells were transduced and selected using puromycin.

Statistical Analysis

Statistical analysis was performed using the InStat statistical program for Macintosh computers. Data were analyzed for statistical significance using Student T test. P values <0.05 were considered significant.

Example 2

Cryptic RGD Containing Peptides from Collagen Type-1 Support Cell Adhesion

Studies have documented the capacity of extracellular matrix (ECM) proteins containing the short amino acid sequence RGD to support interactions mediated by integrin receptors (33). The ability of cells to interact with RGD sites within the context of larger glycoproteins depends on many factors, some of which include the adjacent flanking sequences surrounding the core RGD tri-peptide as well as the geometrical configuration of the intact molecule and how these molecules are oriented within the context of the interconnected network of other ECM proteins (24,25,33). Flanking sequences immediately C-terminal to the RGD site can govern integrin selective binding (24,25,33). RGD motifs can be cryptic and inaccessible to cell surface receptors as is illustrated in the case of triple helical collagen (34). In this regard, five different cryptic RGD containing sites exist within human collagen type-I, each with distinct flanking sequences (Table 1).

TABLE 1

RGD containing epitopes of collagen type-I.

| Peptide | AA Sequence | Location |
|---|---|---|
| P-1 | KGDRGDAPG | Col1a1 742-750 |
| P-2 | QGPRGDKGE | Col1a1 1090-1098 |
| P-3 | AGSRGDGGP | Col1a2 774-782 |
| P-4 | QGIRGDKGE | Col1a2 1002-1010 |
| P-5 | RGPRGDQGP | Col1a2 819-827 |
| P-C | QGPSGAPGE | NA |

Five different cryptic RGD containing sites exist within human collagen type-I, each with distinct flanking sequences. Synthetic peptides of these five sequences were generated and designated P-1 through P-5 as shown above. Additionally, a control peptide (P-C) was generated lacking the RGD tri-peptide motif. The sequences in Table 1 correspond to the following SEQ ID NOs.: KGDRGDAPG (SEQ ID NO. 2), QGPRGDKGE (SEQ ID NO. 3), AGSRGDGGP (SEQ ID NO. 12), QGIRGDKGE (SEQ ID NO 13); RGPRGDQGP (SEQ ID NO. 14); and QGPSGAPGE (SEQ ID NO. 15).

RGD Peptides are Capable Supporting Cell Adhesion

Figure 1B:
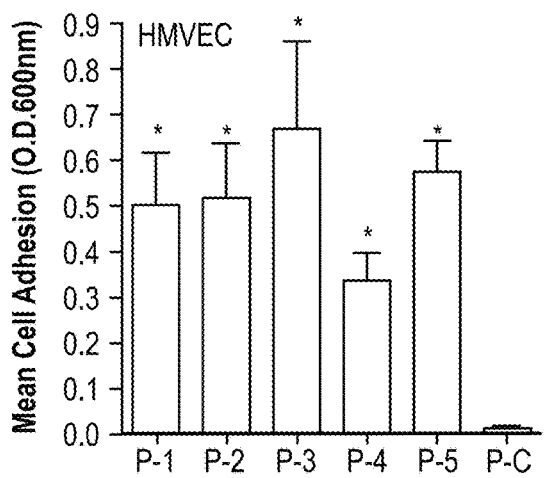
Figure 1C:
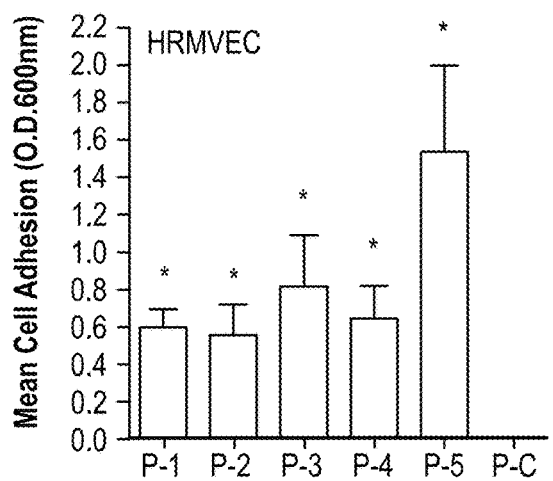
Figure 1D:
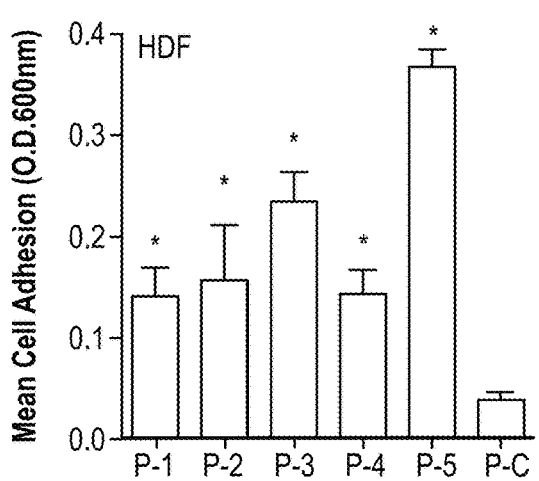

Due to the importance of the RGD tri-peptide motif, the flanking sequences within collagen type-I that surround the core RGD site may alter its cellular recognition were determined. To assess whether these cryptic collagen RGD motifs were redundant or whether the flanking sequences help convey distinct properties, each of the collagen type-I RGD epitopes were synthesized, along with their associated flanking sequences. The five different RGD peptides were immobilized and their ability to facilitate cell adhesion was examined. As shown in FIG. 1A, all five collagen RGD peptides (P1-P5) support human umbilical vein endothelial cell (HUVEC) adhesion, with peptide 5 (P-5) promoting the highest levels of adhesion. In contrast, a peptide control (P-C) in which the RGD motif of P-2 was replaced with SGA failed to support adhesion. To confirm that the adhesion promoting ability was not specific to only HUVECs similar assays were carried out with human microvascular endothelial cells (HMVEC), human retinal microvascular endothelial cells (HRMVEC) and human dermal fibroblasts. All endothelial cells and fibroblast bound the five RGD containing collagen peptides while the control peptide failed to support interactions (FIGS. 1B-1D). These data indicate that while some differences were observed, all five RGD peptides were capable supporting cell adhesion.

Cryptic Collagen RGD Epitopes Using Monoclonal Antibodies

Figure 1E:
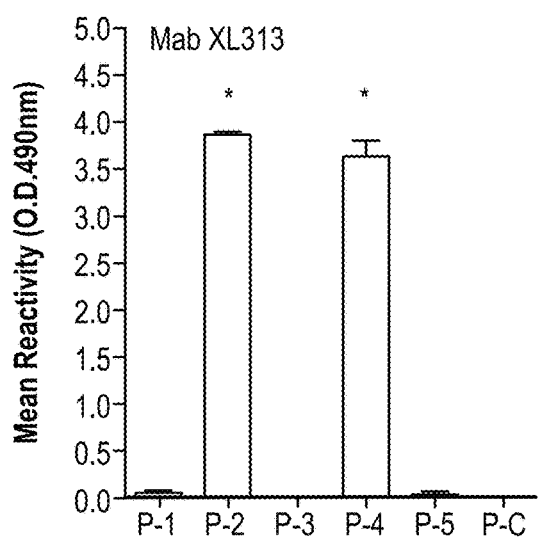
Figure 1F:
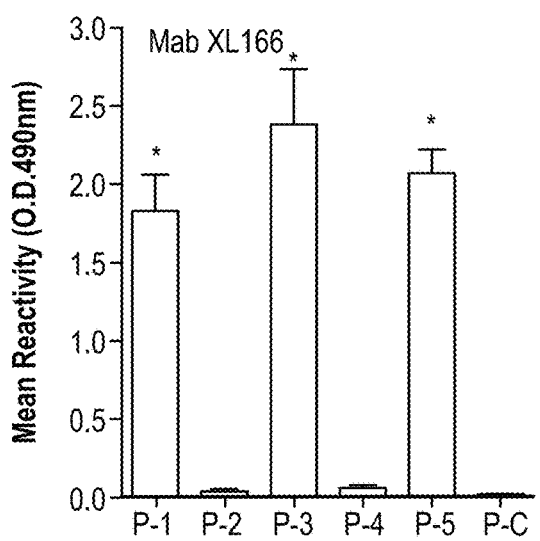

To study these cryptic collagen RGD epitopes, monoclonal antibodies were generated. Two distinct antibodies were isolated with the ability to specifically discriminate between different RGD containing epitopes. As shown in FIG. 1E, Mab XL313 specifically bound to collagen peptides P-2 and P-4 containing the conserved RGDKGE (SEQ ID NO. 1) motif (Table 1), but showed no significant reactivity with other RGD peptides including P-1, P-3 or P-5. A second antibody termed XL166 recognized RGD containing collagen peptides P-1, P-3 and P-5, but failed to bind to the RGDKGE (SEQ ID NO. 1) containing peptides P-2 and P-4 (FIG. 1F). Neither Mab XL313 nor XL166 showed interaction with the control peptide (P-C).

Example 3

XL313 Exhibits Selective Binding for Proteolyzed Collagen Type-I

Figure 2A:
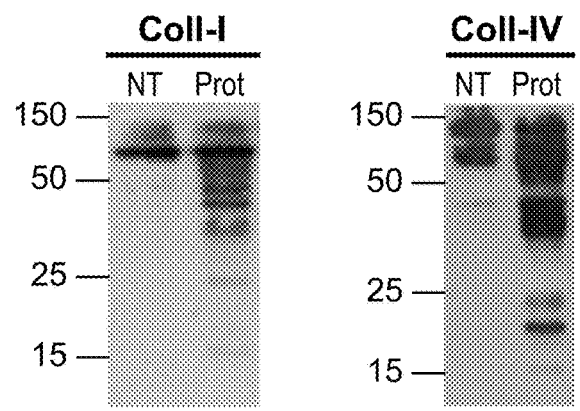
FIGS. 2A-2D is a series of immunoblots and bar graphs depicting that Mab XL313 exhibits selective binding to proteolyzed collagen type-I. Purified collagen type-I and collagen type-IV were incubated with control buffer or activated MMP-2 over a time course and analyzed by Western blot (FIGS. 2A, 2B and 2D) or ELISA (FIG. 2C).
Figure 2B:
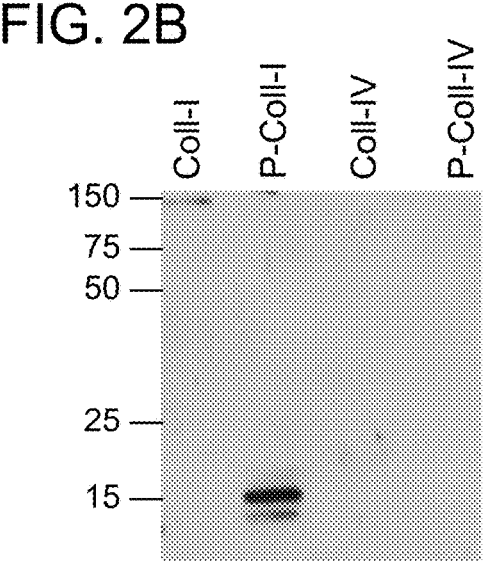
Figure 2C:
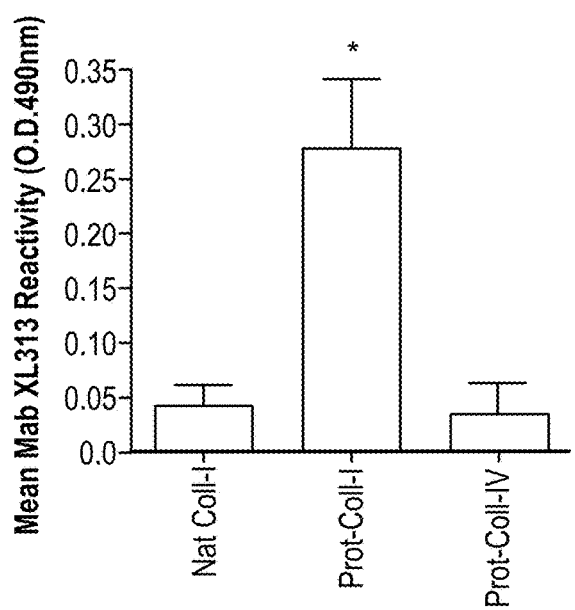

The capacity of Mab XL313 to bind its RGD motif within the context of the full-length collagen molecule was determined. To facilitate these studies, denatured collagen type-1 or IV was incubated with MMP-2 for 12 hrs to generate proteolyzed collagen. MMP-2 mediated proteolysis of collagen type-I and IV resulted in the generation of multiple fragments as indicated by Western blot analysis using antibodies specifically directed to either collagen type-I (FIG. 2A left) or collagen type-IV (FIG. 2A right). Mab XL313 specifically directed to the RGDKGE (SEQ ID NO. 1) collagen sequence exhibited minimal reactivity with intact collagen type I or type IV under denaturing and reducing conditions (FIG. 2B) or under non-denaturing and nonreducing conditions of the ELISA (FIG. 2C). In contrast, Mab XL313 readily detected low molecular weight fragments of collagen type-I, but not collagen type-IV following proteolysis (FIG. 2B). Mab XL313 failed to recognize other RGD containing ECM proteins including vitronectin or fibronectin.

Figure 2D:
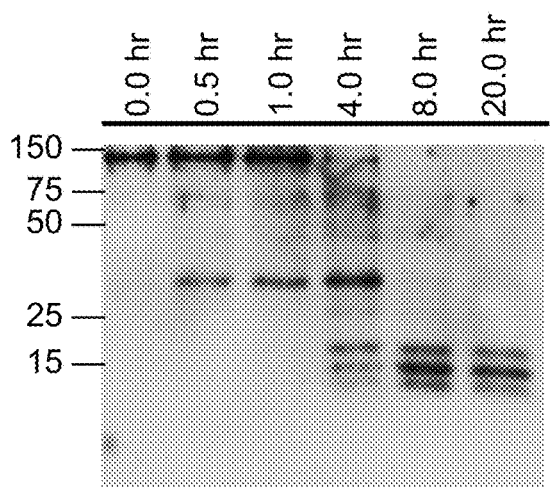

To further examine the generation of the low molecular weight RGDKGE (SEQ ID NO. 1) containing collagen fragments, a time course of MMP-2 mediated collagen proteolysis was examined. MMP-2 mediated degradation of collagen type-I resulted in a time dependent generation of Mab XL313 reactive collagen fragments (FIG. 2D). The majority of the collagen was proteolyzed into Mab XL313 reactive fragments of approximately 14Kd to 16Kd by 8 hours. These findings indicated that XL313 collagen epitopes were cryptic within the intact non-denatured collagen type-1 molecule and that proteolytic degradation was required to efficiently expose the hidden RGDKGE (SEQ ID NO. 1) containing motif.

Example 4

Differential Roles of Cryptic RGD Collagen Motifs on Angiogenesis and Inflammation In Vivo Studies have shown that collagen remodeling within the vascular basement membrane can result in exposure of multiple non-RGD cryptic collagen sites including the HUIV26 and HU177 epitopes that can play active roles in angiogenesis (21,23). Given these findings, it was determined whether distinct RGD containing epitopes were exposed in vivo. First, to examine whether these RGD epitopes could be generated during angiogenesis the chick chorioallantoic membrane (CAM) model (19) was used. The CAMs of chick embryos were stimulated with FGF-2, and the generation of RGD containing collagen epitopes was examined using Mabs XL313 and XL166. As shown in FIG. 3A, little Mab XL313 or XL166 reactive epitope was detected in non-stimulated CAMs. In contrast, RGD containing collagen epitopes (Green) were readily detected in FGF-2 stimulated CAM tissues confirming the differential generation of RGD containing epitopes recognized by these antibodies. Mab XL313 and XL166 reactive RGD epitopes did not exhibit a typical extracellular fibril collagen pattern, but rather exhibited punctate distribution with both intracellular and scattered extracellular localization. The intracellular distribution is similar to the staining pattern of collagen degradation products previously documented within intracellular vesicles of macrophages (35).

Given the generation of these distinct sets of RGD containing epitopes, their active roles in regulating angiogenesis and inflammation were examined. Angiogenesis was induced within the CAMs of 10-day old chick embryos with FGF-2 using filter discs coated with cortisone acetate (CA) to reduce growth factor associated inflammation. As shown in FIG. 3B, treatment with Mab XL313 directed to the cryptic RGDKGE (SEQ ID NO. 1) containing epitope (P<0.05) inhibited FGF-2 induced angiogenesis by greater than 75% as compared to non-treated or control antibody. Mab XL166 that specifically binds the remaining three cryptic RGD collagen peptides (P-1, P-3, and P-5) had no effect. These findings were consistent with the notion that while distinct RGD containing collagen epitopes were readily generated in vivo, were not functionally redundant.

FGG-2 Induced Inflammation is Associated with Recruitment and Accumulation of Granulation-Tissue Associated Macrophages.

The chick CAM has been routinely used to assess inflammation and granulation tissue formation, which are largely dependent on infiltration of chick heterophils (the avian equivalent of neutrophils), macrophages and activated fibroblasts (36,37). To study the potential differential biological impact of RGD epitopes, FGF-2 induced inflammation was examined by carrying out similar experiments in the absence of cortisone acetate and quantifying CAM thickening. As shown in FIG. 3C, treatment with FGF-2 induced CAM inflammation as indicated by robust tissue thickening (top panels), extensive infiltration of inflammatory infiltrates as indicated by Giemsa stain (middle panel) and increased accumulation of monocytes and macrophages (bottom panel) following staining with an antibody directed to avian specific monocytes and macrophages. Macrophage infiltration of the CAMs stimulated with FGF-2 was (P<0.05) enhanced over 2-fold as compared to control (FIG. 3D) indicating that FGF-2 induced inflammation in this model is associated with the recruitment and accumulation of granulation-tissue associated macrophages.

FGF-2 Induced Inflammatory Response in the Presence or Absence of Anti-RGD Specific Antibodies of XL313 and XL166

To examine whether the RGD containing collagen epitopes play a role in the FGF-2 stimulated inflammatory response, this FGF-2 induced inflammatory response was examined in the presence or absence of anti-RGD specific antibodies XL313 and XL166. Quantification indicated that FGF-2 stimulation in the absence of cortisone acetate resulted in approximately 50% of the CAMs showing robust formation of thick granulation tissue (FIG. 3E). Treatment of CAMs with cortisone acetate, a well document anti-inflammatory agent significantly (P<0.05) reduced the percentage of CAMs exhibiting thickening by greater than 80% as compared to either no treatment or control antibody. Interestingly, treatment of CAMs with Mab XL313 also (P<0.05) inhibited the number of CAMs exhibiting inflammation by approximately 75% as compared to controls. In contrast, treatment of CAMs with Mab XL166 showed no significant (P>0.05) impact. These data are consistent findings while examining angiogenesis indicating a differential role for specific cryptic RGD epitopes in vivo.

Example 5

Generation of XL313 Cryptic RGDKGE (SEQ ID NO. 1) Epitope

During angiogenesis and inflammation, multiple cell types including endothelial cells, fibroblasts and macrophages proteolytically remodel extracellular collagen creating a permissive microenvironment that facilitates stromal cell infiltration and new blood vessel growth. A variety of cells including fibroblasts and endothelial cells express collagen and, partially degraded collagen can be internalized and further processed by activated M2-like macrophages leading to the generation of low molecular weight fragments (35,38). Because of the unique pattern of Mab XL313 immunoreactivity observed in vivo, it was determined whether stromal cells associated with angiogenesis and inflammation could generate the RGDKGE (SEQ ID NO. 1) containing epitope. Whole cell lysates were prepared from fibroblasts and endothelial cells and Western blots were performed. While some Mab XL313 reactive species was detected in lysates of endothelial cells and fibroblasts, the major immunoreactive species migrated between approximately 75Kd to 28Kd indicating that these species were unlikely to represent intact collagen. In addition, minimal amounts of low molecular weight species were detected that corresponds to the major 14Kd to 16Kd collagen fragments detected following MMP-2 mediated proteolysis. While a small amount of an approximately 20 Kd XL313 reactive species was detected in serum free conditioned medium (CM) collected from HUVECS, no significant levels of immunoreactive fragments in fibroblast CM was detected.

Given the minimal reactivity observed in these cell types known to express collagen, and that FGF-2 induced a strong angiogenic and inflammatory response in CAMs that was associated with an extensive infiltration of macrophages, FGF-2 treated CAM tissues for the co-distribution of the XL313 epitope and macrophages was examined. As shown in FIG. 4B, the XL313 reactive epitope (Red) co-localized with a subset of macrophages (Green) in FGF-2 stimulated CAMs, indicating that macrophages may be one source of the XL313 collagen epitope. To study this possibility, both whole cell lysates (FIG. 4C left) and serum free CM (FIG. 4C right) from three different macrophage-like cell lines were examined. In contrast, to endothelial cells and fibroblasts, strong immunoreactive species were readily detected in cell lysates and CM from multiple macrophage cell lines including Raw 264.7, THP1 and BV2. Importantly, low molecular weight immunoreactive species migrating between 14Kd to 16Kd were readily detected in serum free CM (FIG. 4C right). These 14Kd to 16Kd immunoreactive species corresponded to the size of low molecular weight Mab XL313 reactive collagen fragments detected following MMP-mediated proteolytic digestion of purified collagen. To further study the XL313 immunoreactive species detected in macrophages, the generation of the 14Kd to 16Kd RGDKGE (SEQ ID NO. 1) containing XL313 fragments in Raw 264.7 macrophages was examined. First, to examine the expression of collagen in these macrophages, the expression of mRNA for the alpha 1 and alpha 2 chains of collagen type-I in RAW macrophages by PCR was confirmed. Secondly, while no full length collagen type-I was detected in either cell lysates or CM from macrophages using anti-collagen type-I specific antibodies, low molecular weight fragments migrating at the same molecular weight as the RGDKGE (SEQ ID NO. 1) containing epitope in both cell lysates and CM using either Mab XL313 or an anti-collagen-I specific antibody (FIG. 4D) was detected. Importantly, shRNA-mediated knockdown of the alpha 2 chain of collagen type-I reduced immune-detection of the low molecular species (14Kd to 16Kd) in both lysates and CM when using either anti-collagen specific antibodies or Mab XL313 (FIG. 4D). Together, these findings were consistent with the possibility that macrophages were one cellular source of the RGDKGE (SEQ ID NO. 1) collagen epitope.

Example 6

Figure 5A:
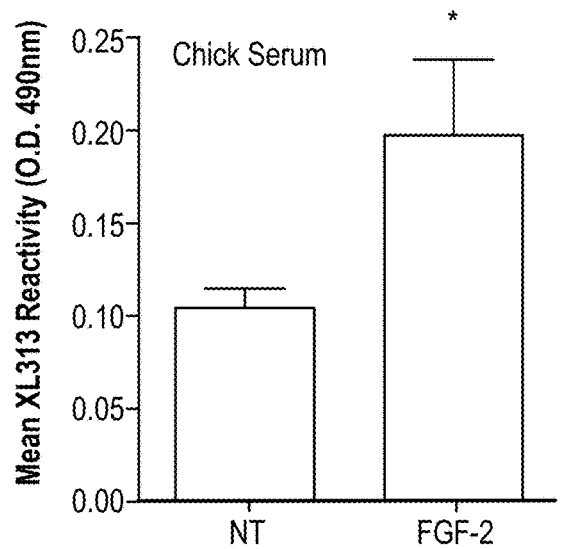
FIGS. 5A-5D are bar graphs depicting the induction of angiogenesis and inflammation in vivo by soluble RGDKGE (SEQ ID NO. 1) but not a related RGDAPG (SEQ ID NO. 11) containing collagen epitope.

Induction of Angiogenesis and Inflammation In Vivo by Soluble RGDKGE (SEQ ID NO. 1) but not a Related RGDAPG (SEQ ID NO. 11) Containing Collagen Epitope Due to the differential expression and bio-distribution of the RGDKGE (SEQ ID NO. 1) epitope in angiogenic CAM tissues and its expression in macrophage-conditioned medium, it was determined whether a soluble circulating form of this RGDKGE (SEQ ID NO. 1) epitope could be generated. To examine this possibility, chick embryos were either un-treated or stimulated with FGF-2 and serum, and collected three days later. As shown in FIG. 5A, low levels of circulating Mab XL313 immunoreactive epitope was detected in the serum from non-stimulated control chick embryos. In contrast, a ($P<0.05$) 2-fold increase was detected in the levels of circulating XL313 epitope following FGF-2 stimulation. These findings indicated the differential release of a soluble form of this RGDKGE (SEQ ID NO. 1) containing collagen epitope.

Figure 5B:
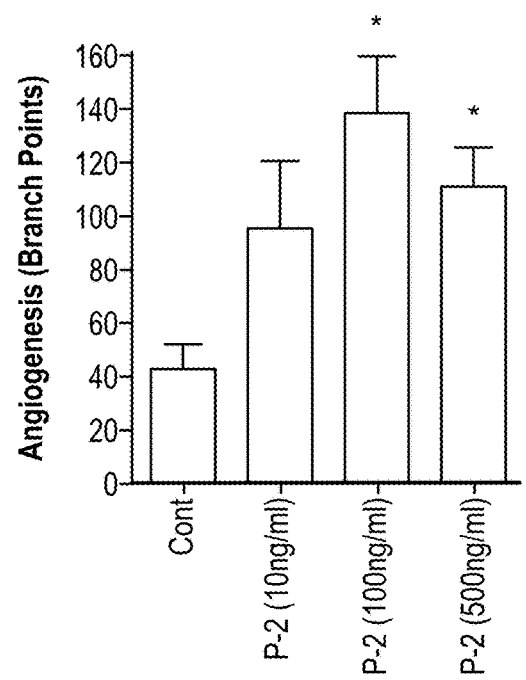
Figure 5C:
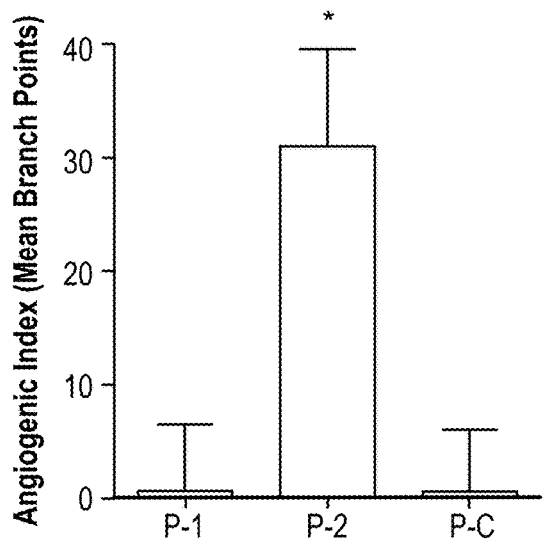

Soluble Peptide Containing the XL313 Epitope Actively Regulates Angiogenesis and Inflammation Because a soluble form of the RGDKGE (SEQ ID NO. 1) epitope was detected in vivo, it was next determined whether a soluble peptide containing the XL313 epitope actively regulated angiogenesis and inflammation. To examine this possibility, the effects of the RGDKGE (SEQ ID NO. 1) containing collagen peptide on angiogenesis and inflammation in the chick CAM were assessed. As shown in FIG. 5B, the XL313 RGDKGE (SEQ ID NO. 1) containing collagen peptide (P-2) dose dependently enhanced angiogenesis with maximum induction observed at a dose of 100 ng/CAM. Stimulation of CAMs with the RGDKGE (SEQ ID NO. 1) containing collagen peptide P-2, but not the related RGDAPG (SEQ ID NO. 11) containing collagen peptide P-1, or peptide control (P-C) significantly ($P>0.05$) induced angiogenesis as compared to no treatment (FIG. 5C).

Figure 5D:
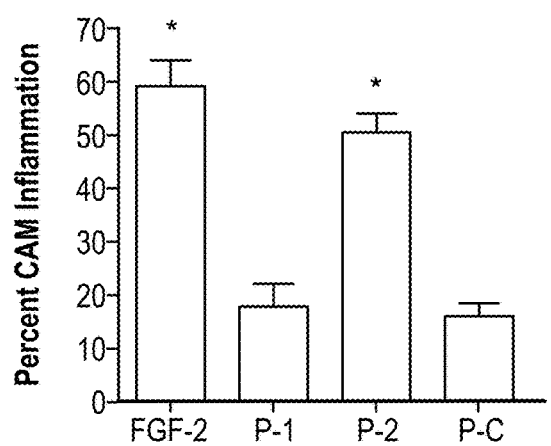

The effects of the soluble RGD containing collagen peptides on inflammation were examined. As shown in FIG. 5D, FGF-2 induced a strong inflammatory response in the chick CAM in the absence of cortisone acetate as indicated by approximately 55%-60% of the CAMs exhibiting extensive tissue thickening. Minimal evidence of tissue inflammation was observed following stimulation with either control peptide (P-C) or the RGDAPG (SEQ ID NO. 11) containing collagen peptide P-1, while the RGDKGE (SEQ ID NO. 1) collagen peptide P-2 significantly ($P<0.05$) induced inflammation to nearly that of FGF-2 stimulation (FIG. 5D). These studies indicated that the biological impact of RGD containing collagen peptides on angiogenesis and inflammation in the chick CAM depended on their associated flanking sequences.

Example 7

Figure 6A:
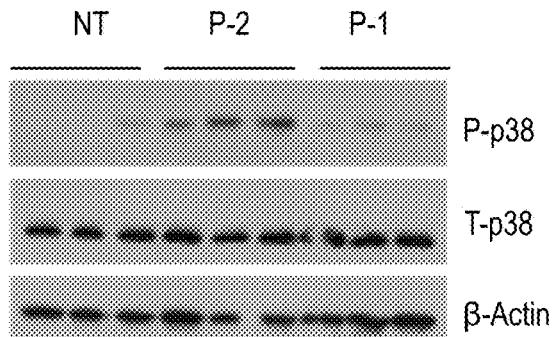
FIG. 6A-6F are data depicting RGDKGE (SEQ ID NO. 1) containing collagen peptide P-2 induced angiogenesis depends on P38MAPK. Angiogenesis was induced within the chick CAMs and the relative level of P38MAPK was assessed.
Figure 6B:
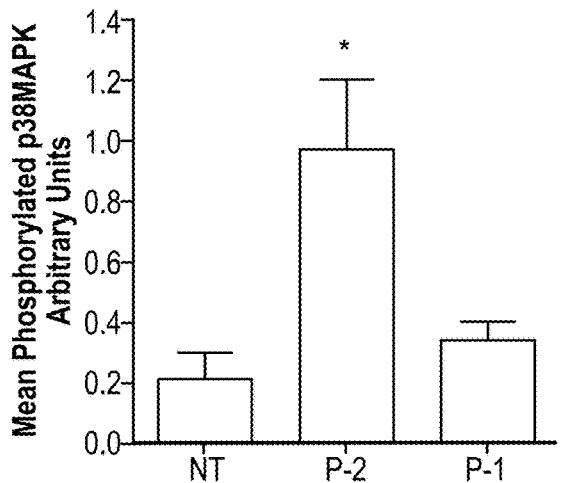
Figure 6C:
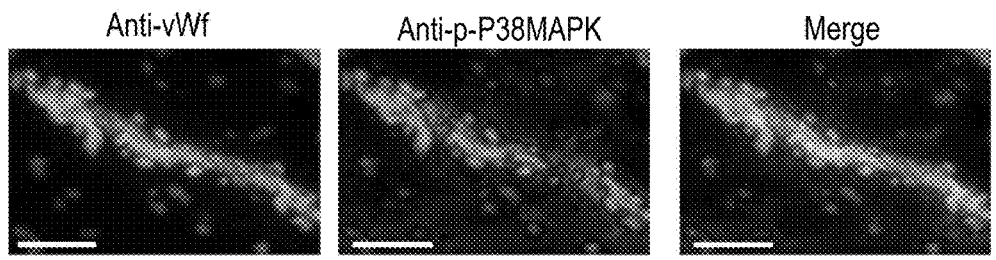

RGDKGE (SEQ ID NO. 1) Containing Peptide P-2 Induced Angiogenesis Depends on P38MAPK Studies have indicated that angiogenesis and inflammation in the chick CAM is associated with alterations in MAP kinase signaling including P38MAPK (40,41). To examine mechanisms that regulate angiogenesis following stimulation with the RGDKGE (SEQ ID NO. 1) containing collagen peptide P-2, CAM tissues from untreated or RGD peptide treated animals was examined. As shown in FIG. 6A, elevated levels of phosphorylated P38MAPK were detected in lysates from CAMs treated with RGDKGE (SEQ ID NO. 1) containing peptide P-2 as compared to either untreated or RGDAPG (SEQ ID NO. 11) containing peptide P-1 treated animals. Quantification of CAM tissues (N=12) indicated a $P<0.05$ 4-fold increase in phosphorylation of P38MAPK as compared to controls (FIG. 6B). Consistent with studies, while activated P38MAPK was detected in multiple cell types in chick CAMs, co-staining analysis indicated expression of phosphorylated P38MAPK in vWf positive blood vessels (FIG. 6C).

Figure 6D:
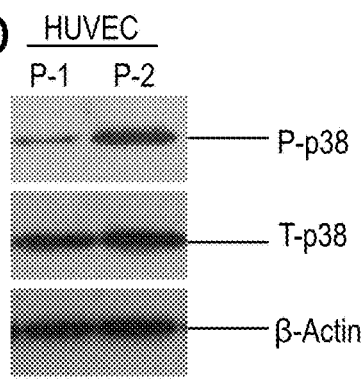
Figure 6E:
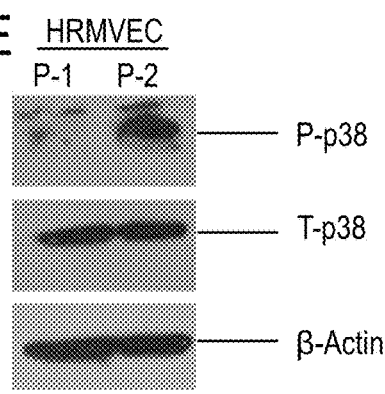
Figure 6F:
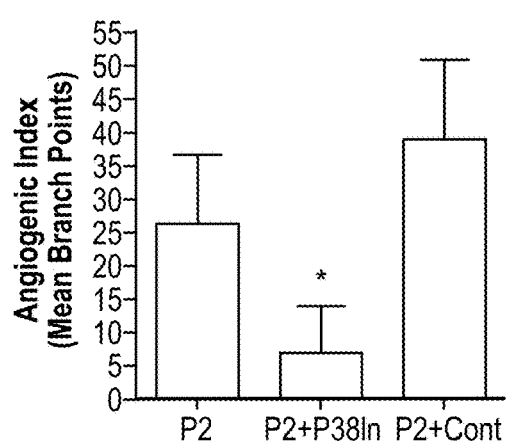

The effects of the RGD containing collagen peptides on the levels of phosphorylated P38MAPK in endothelial cells were examined. As shown in FIGS. 6D and 6E, while both RGD containing collagen peptides P-1 and P-2 support cell binding, interactions with RGDKGE (SEQ ID NO. 1) collagen peptide P-2 resulted in enhanced phosphorylation of P38MAPK as compared to RGDAPG (SEQ ID NO. 11) collagen peptide P-1 in HUVECs (FIG. 6D) or HRMVEC (FIG. 6E). A functional role for P38MAPK in mediating RGDKGE (SEQ ID NO. 1) peptide P-2 induced angiogenesis in vivo was demonstrated as P-2 induced angiogenesis was (P<0.05) reduced by P38MAPK inhibitor (FIG. 6F). Together, these data indicate a role for P38MAPK in the peptide P-2 stimulated pro-angiogenic response observed in vivo.

Example 8

Figure 7A:
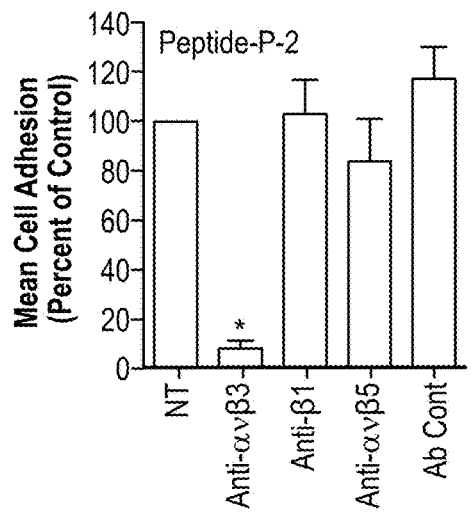
FIGS. 7A-7G are images depicting collagen peptide P-2 binds and activates αvβ3 and stimulates P38MAPK activation in a Src dependent manner.
Figure 7B:
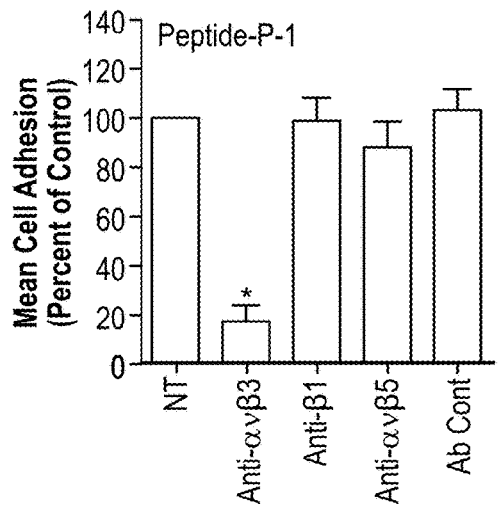

Collagen Peptide P-2 Binds and Activates αvβ3 and Stimulates P38MAPK Activation in a Src Dependent Manner It is well established that multiple integrins recognize RGD amino acid motifs within ECM proteins. However, the ability of an integrin to bind distinct RGD epitopes depends in part on its orientation within the parent molecule and the C-terminal amino acid sequences flanking the RGD motif (25-27). Potential cell surface receptors that mediate interactions with the RGDKGE (SEQ ID NO. 1) containing collagen P-2 peptide were identified. The ability of endothelial cells to bind the RGD collagen peptides P-1 and P-2 in the presence or absence of function blocking anti-integrin antibodies was examined. As shown in FIG. 7A, anti-β1 specific antibody had minimal effect on HUVEC adhesion to peptide P-2 while anti-αvβ3 antibody (P<0.05) inhibited interactions by approximately 90% as compared to control. Anti-αvβ5 antibody showed little inhibition. Similar results were observed with P-1, which contains the RGDAPG (SEQ ID NO. 11) sequence (FIG. 7B). These data indicate that αvβ3 functions as a receptor for both RGD containing peptides in endothelial cells.

RGD Peptides Differentially Altered αvβ3-Mediated Signaling

Figure 7C:
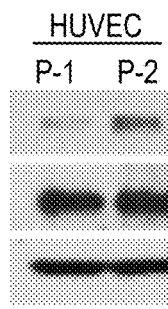
Figure 7D:
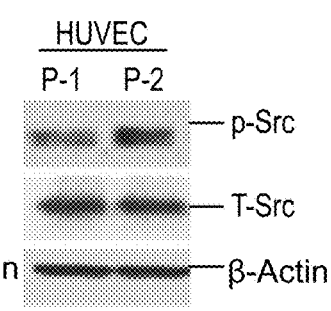
Figure 7E:
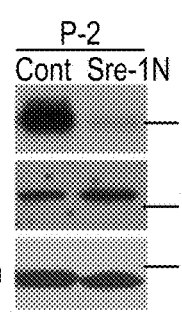
Figure 7F:
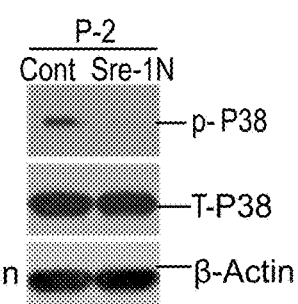
Figure 7G:
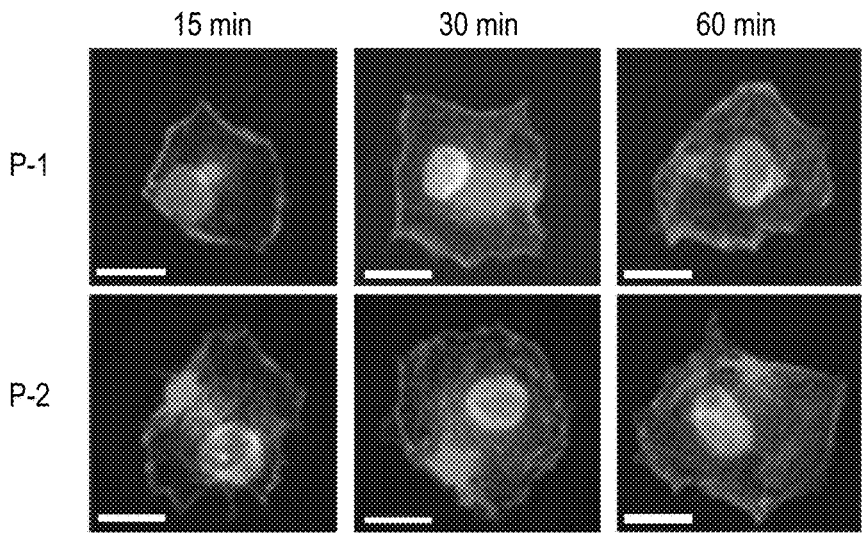

Because both RGD containing peptides bind αvβ3 coupled with the differential effect of these peptides on angiogenesis and inflammation, it was determined whether the RGD peptides differentially altered αvβ3-mediated signaling. Endothelial cells were allowed to attach to P-1 and P-2 and the relative level of β3-integrin phosphorylation was examined. As shown in FIG. 7C, in the absence of any growth factors, β3 phosphorylation (P<0.05) increased over 3-fold following ligation of RGDKGE (SEQ ID NO. 1) peptide P-2, as compared to RGDAPG (SEQ ID NO. 11) peptide P-1. Ligand binding of β3 integrin induced receptor clustering and initiated down-stream signaling events including activation of protein kinases including Fak and Src. Therefore, the differential phosphorylation of these protein kinases following the early mechanical-mediated interactions with the RGD containing collagen peptides was assessed. Minimal Fak phosphorylation was detected following ligation of either P-1 or P-2 under these serum free conditions. In contrast, Src phosphorylation was enhanced by nearly 2-fold following interactions with P-2 as compared to P-1 (FIG. 7D). Moreover, activation of β3 integrin and P38MAPK in endothelial cells following binding to P-2 was dependent on Src as incubation of endothelial cells with a Src inhibitor reduced β3 and P38MAPK phosphorylation following binding to collagen peptide P-2 (FIGS. 7E and 7F). Activation of Src and P38MAPK leads to enhanced actin polymerization and stress fiber formation (43-45), therefore the actin cytoskeleton in endothelial cells following binding to the RGD collagen peptides was examined. Endothelial cell interactions with the RGDKGE (SEQ ID NO. 1) collagen peptide P-2 resulted in accelerated actin stress fiber formation as compared to interactions with RGDAPG (SEQ ID NO. 11) collage peptide P-1 (FIG. 7G). Cumulatively, these findings indicate the ability of the conserved RGDKGE (SEQ ID NO. 1) collagen epitope to stimulate initiation of a β3-integrin dependent mechano-transduction pathway.

Example 9

Figure 8A:
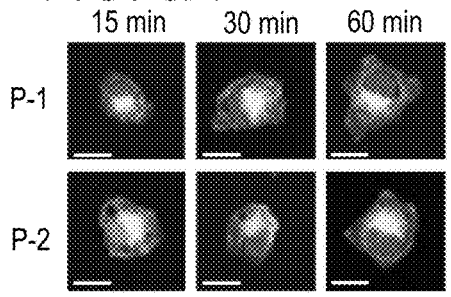
FIGS. 8A-8I are data depicting that cellular interactions with RGDKGE (SEQ ID NO. 1) collagen-containing peptide accelerates actin stress fiber formation and nuclear YAP accumulation promoting endothelial growth.
Figure 8B:
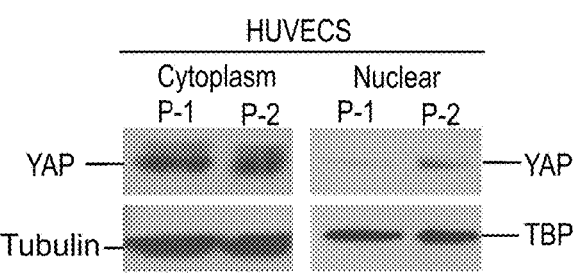

Cellular Interactions RGDKGE (SEQ ID NO. 1) Containing Peptide Enhances Nuclear YAP Accumulation and Endothelial Cell Growth The data indicate that while both RGD containing collagen peptides P-1 and P-2 support an initial β3-integrin-mediated endothelial cell adhesive interaction, collagen peptide P-2 selectively enhanced β3-integrin phosphorylation leading to increased activation of P38MAPK and accelerated actin stress fiber formation. Actin stress fiber formation and enhanced mechanical tension contribute to re-localization of the transcriptional co-activator Yes-associated protein (YAP) to the nucleus (46). Moreover, YAP is implicated in regulating angiogenesis and endothelial cell growth (47, 48). YAP localization following endothelial cell binding to the distinct collagen RGD containing peptides in the absence of growth factor stimulation was examined. As shown in FIG. 8A, enhanced level of nuclear localized YAP was detected by 15 minutes following endothelial cell binding to collagen peptide P-2 as compared to P-1. The differential nuclear localization of YAP was not consistently detected at later time points. To confirm this enhanced nuclear accumulation of YAP, Western blot analysis was carried out. As shown in FIG. 8B, the levels of nuclear YAP increased by approximately 2-fold in endothelial cells attached to the peptide P-2 as compared to peptide P-1.

Effects of RGD Containing Collagen Peptides on HUVEC and HRMVEC Growth

Figure 8C:
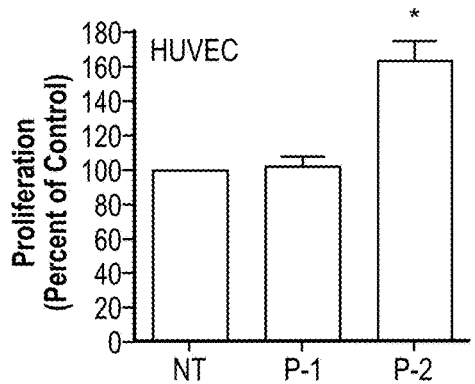
Figure 8D:
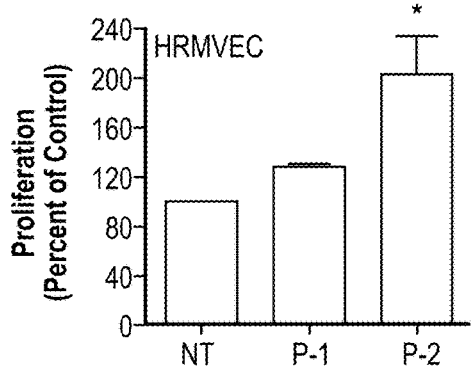
Figure 8E:
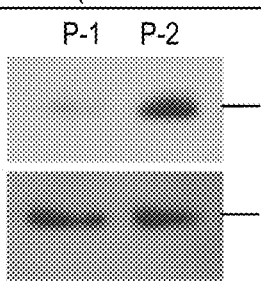
Figure 8F:
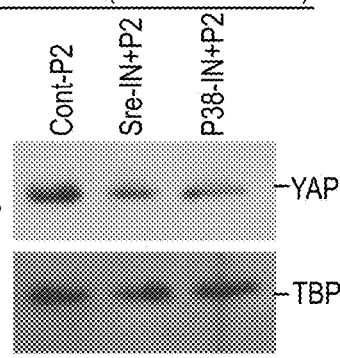

Nuclear localization of YAP contributes to the regulation of endothelial cell growth. Therefore, the effects of RGD containing collagen peptides on HUVEC and HRMVEC growth were examined. Addition of soluble P-2 significantly (P<0.05) enhanced endothelial cell growth while stimulation with RGDAPG (SEQ ID NO. 11) peptide P-1 had a minimal effect (FIGS. 8C and 8D). The selective ability of P-2 to enhance Src-dependent activation of P-38MAPK, the ability of the enhanced nuclear accumulation of YAP following RGDKGE (SEQ ID NO. 1) peptide P-2 stimulation was Src-dependent and/or P38MAPK dependent was assessed. As shown in FIGS. 8E and 8F, nuclear YAP accumulation following P-2 stimulated endothelial cells was reduced by approximately 50% by treatment with either Src or P38MAPK inhibitors as compared to control. These data are consistent with a role for Src and P38MAPK in mediating the RGDKGE (SEQ ID NO. 1) P-2 stimulated nuclear accumulation of YAP.

P-2 Stimulated Endothelial Cell Growth Depends on YAP

Figure 8G:
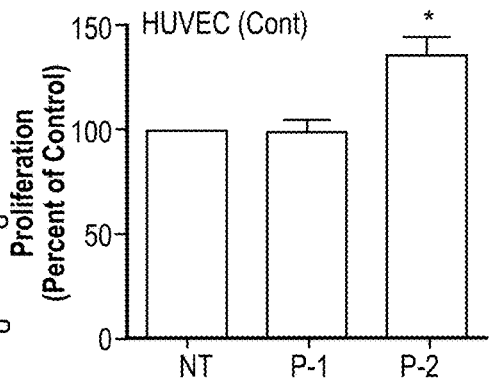
Figure 8H:
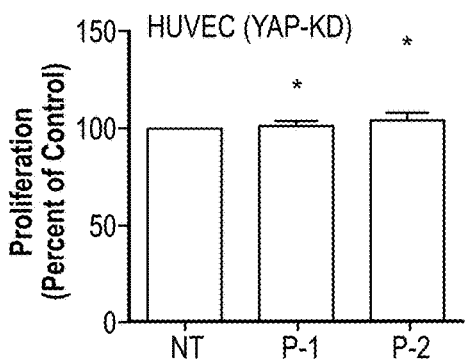
Figure 8I:
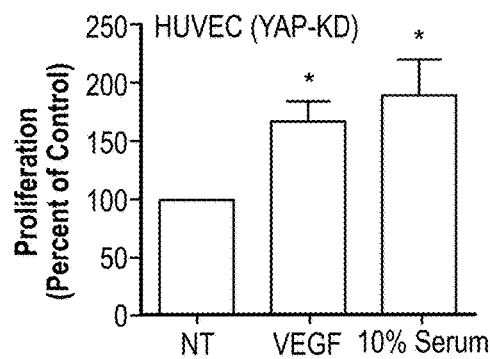

YAP plays roles in regulating the expression of multiple angiogenesis and inflammatory factors; therefore it was examined whether P-2 stimulated endothelial cell growth depends on YAP. Endothelial cells with YAP specific or non-specific shRNAs were transduced. Addition of soluble RGDKGE (SEQ ID NO. 1) containing collagen peptide P-2 to endothelial cells, but not the related RGDAPG (SEQ ID NO. 11) containing peptide P1, (P<0.05) enhanced growth in control transduced cells (FIG. 8G), while the RGDKGE (SEQ ID NO. 1) peptide P-2 failed to induce growth in endothelial cells in which YAP was knocked down (FIG. 8H). YAP knock down cells were capable of proliferating as enhanced growth was observed following VEGF or high serum stimulation (FIG. 8I). Together, the findings are consistent with a mechanism by which RGDKGE (SEQ ID NO. 1) containing collagen peptide P-2 initiated a unique mechano-signaling cascade leading to the activation of P38MAPK in a Src-dependent pathway that ultimately led to nuclear YAP accumulation and enhanced endothelial cell growth.

Example 10

Enhanced Expression of PDL-1 in Human M21 Melanoma Tumors as Compared to M21L Melanoma Tumors Lacking αvβ3

Figure 10:
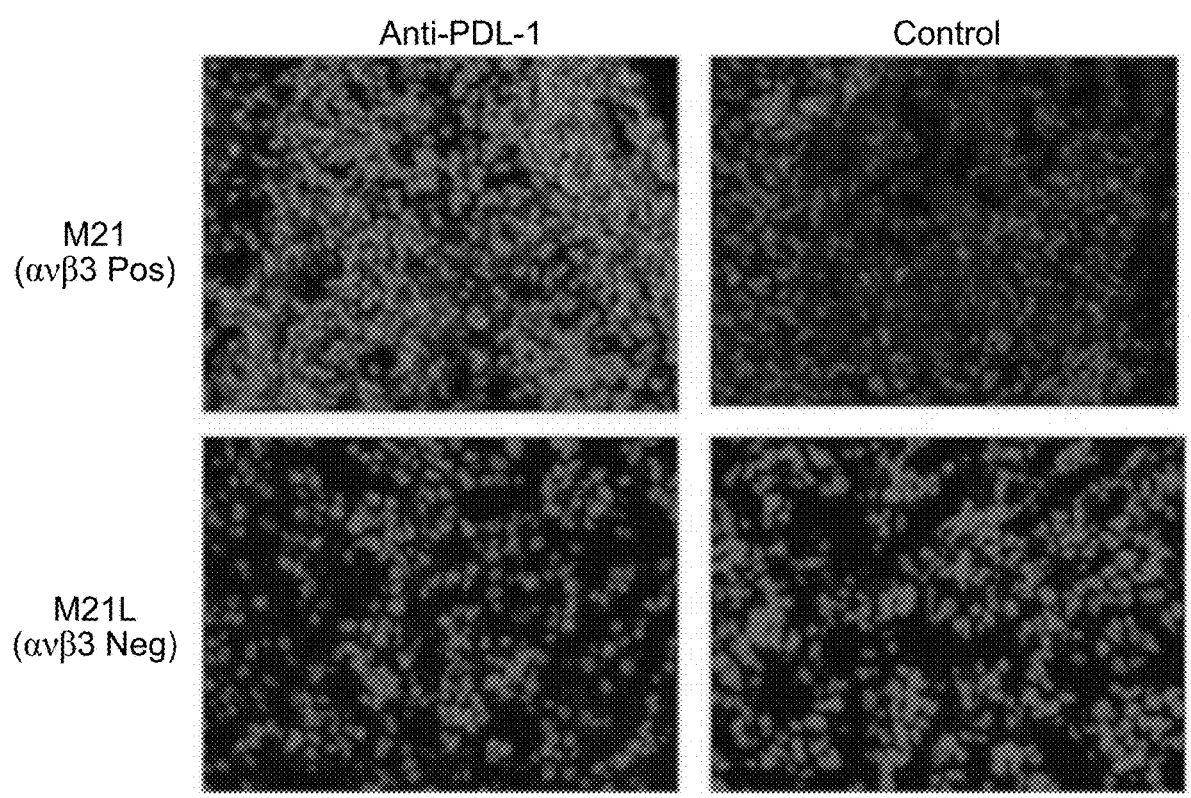
FIG. 10 are images depicting that enhanced expression of PDL-1 in human M21 melanoma tumors as compared to M21L melanoma tumors lack αvβ3. Mice (nude) were injected with either M21 (αvβ3+) or M21L (αvβ3−) melanoma cells. Mice were allowed to establish pre-existing tumors. Mice were sacrificed and tumors dissected and snap frozen. Tumor sections were analyzed for expression of the immune checkpoint regulatory protein PDL-1 by immunofluorescence staining. Red color indicates expression of PDL-1. Control indicates staining with secondary antibody only.

Nude mice were injected with either M21 (αvβ3+) or ML21 (αvβ3−) melanoma cells and were allowed to establish pre-existing tumors. Tumor sections were analyzed for expression of the immune checkpoint regulatory protein PDL-1 by immunofluorescence staining (FIG. 10).

Example 11

Figure 11:
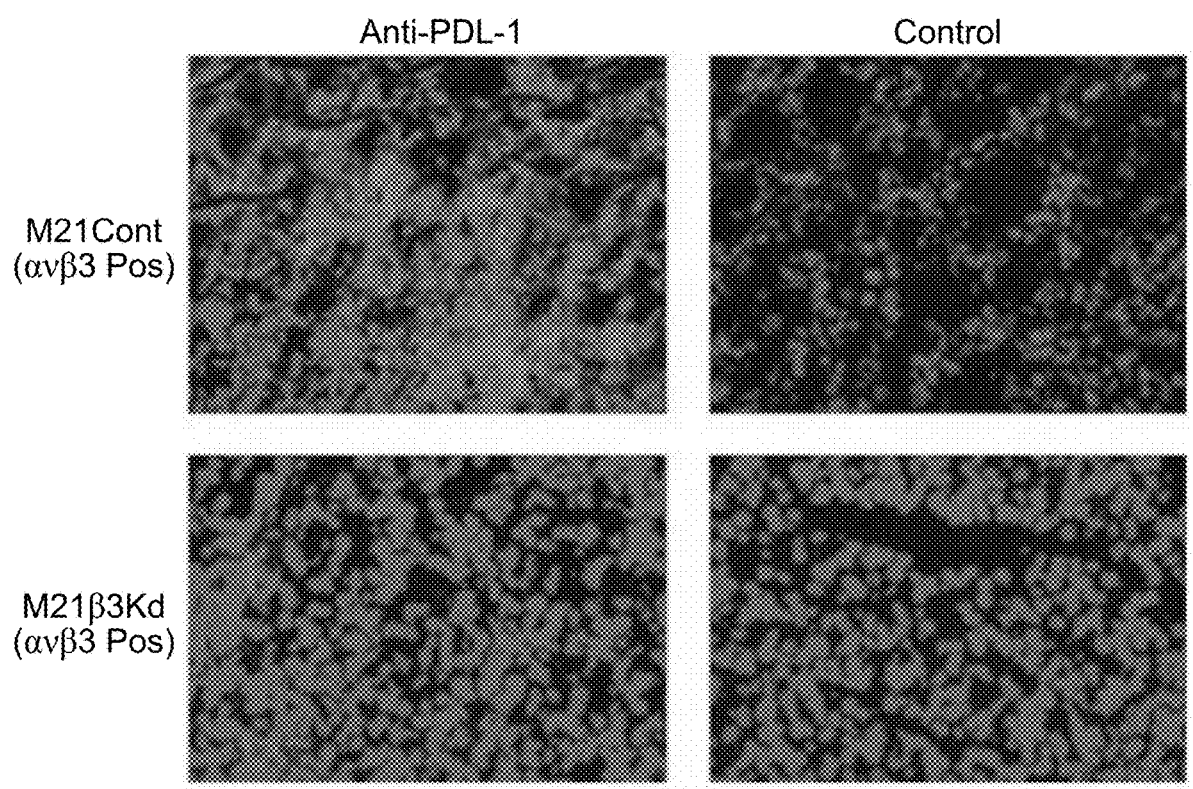
FIG. 11 are images depicting enhanced expression of PDL-1 in human M21 melanoma tumors as compared to M21 melanoma tumors in which β3 integrin was knocked down. M21 melanoma cells that express integrin αvβ3 were transfected with non-specific control shRNA (M21 Cont) or β3 specific shRNA (M21β3Kd). Mice (nude) were injected with either M21 Cont (αvβ3+) or M21β3Kd (αvβ3−) melanoma cells. Mice were allowed to establish pre-existing tumors. Mice were sacrificed and tumors dissected and snap frozen. Tumor sections were analyzed for expression of the immune checkpoint regulatory protein PDL-1 by immunofluorescence staining. Red color indicates expression of PDL-1. Control indicates staining secondary antibody only.

Enhanced Expression of PDL-1 in Human M21 Melanoma Tumors as Compared to M21 Melanoma Tumors in which β3 Integrin was Knocked Down M21 melanoma cells that express integrin αvβ3 were transfected with non-specific control shRNA (M21 Cont) or β3 specific shRNA (M21β3Kd) (FIG. 11). Nude mice were injected with either M21 Cont (αvβ3+) or M21β3Kd (αvβ3−) melanoma cells and were allowed to establish pre-existing tumors. Tumor sections were analyzed for expression of the immune checkpoint regulatory protein PDL-1 by immunofluorescence staining.

Example 12

Figure 9:
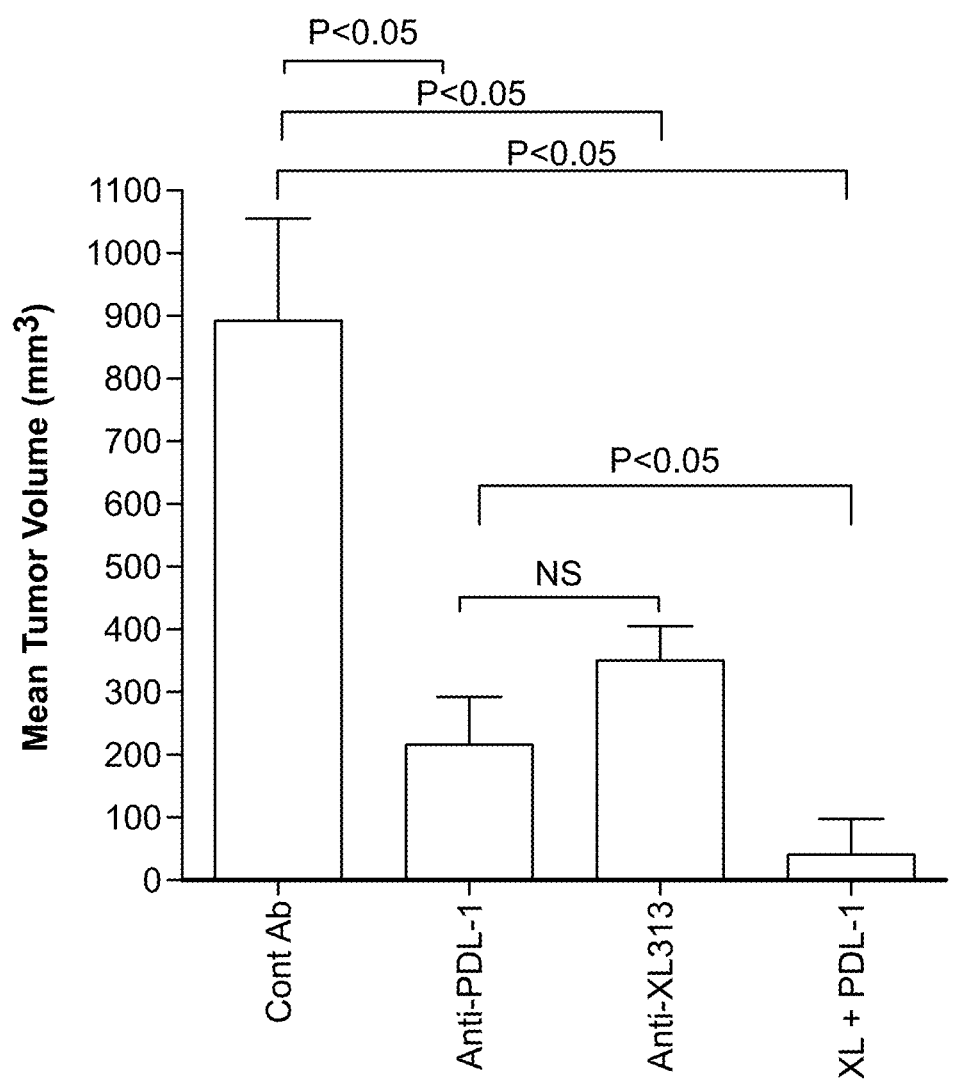
FIG. 9 is a bar graph depicting that Mab XL313 enhances the anti-tumor activity of the immune checkpoint inhibitor for anti-PDL-1 antibody. Mice (C57BL/6) were injected with 3.5×10⁵ B16F10 melanoma cells. Mice were allowed to establish pre-existing tumors for 5 days prior to treatment. Mice were treated (100 μg/mouse) 3 times per week for 14 days. Data represents mean tumor volume at day 14±SE from 8 mice per condition. P<0.05 was considered significant.

MabXL313 Enhanced the Anti-Tumor Activity of the Immune Checkpoint Inhibitor Anti-PDL-1 Antibody Mice were injected with B16F10 melanoma cells and were allowed to establish pre-existing tumors for 5 days prior to treatment (FIG. 9). Data in FIG. 9 represent mean tumor volume at day 14±SE from 8 mice per condition.

Example 13

Reduced Expression of PDL-1 in Melanoma Tumors in Mice Treated with an Antibody Targeting the αvβ3 Ligand (RGDKGE (SEQ ID NO. 1) Containing XL313 Collagen Epitope)

Figure 12:
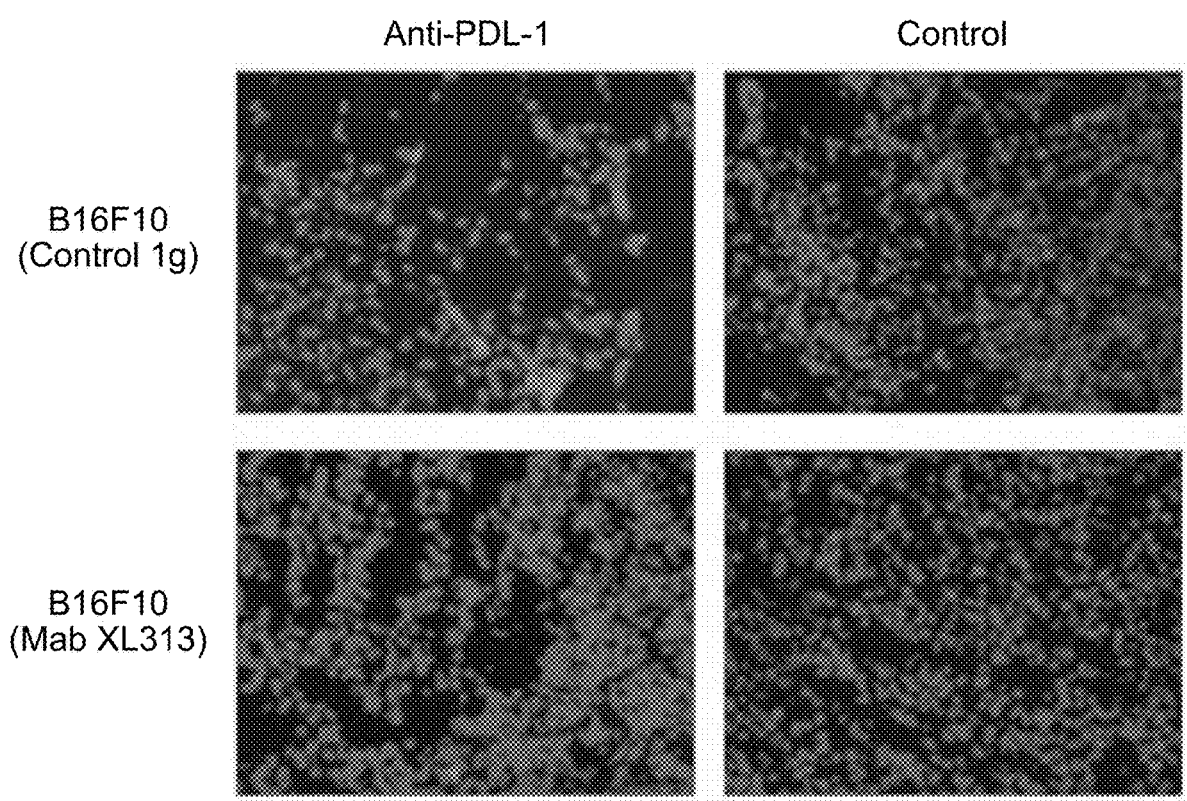
FIG. 12 are images depicting reduced expression of PDL-1 in Melanoma tumors in mice treated with an antibody targeting the αvβ3 ligand (RGDKGE (SEQ ID NO. 1) containing XL313 collagen epitope). Mice (C57BL/6) were injected with 3.5×10⁵ B16F10 melanoma cells. Mice were allowed to establish pre-existing tumors for 5 days prior to treatment. Mice were treated (100 μg/mouse) 3 times a week for 14 days with an antibody targeting the αvβ3 binding RGDKGE (SEQ ID NO. 1) containing collagen epitope. Mice were sacrificed and tumors dissected and snap frozen. Tumor sections were analyzed for expression of the immune checkpoint regulatory protein PDL-1 by immunofluorescence staining. Red color indicates expression of PDL-1. Control indicates staining with secondary antibody only.

Mice were injected with melanoma cells and were allowed to establish pre-existing tumors for 5 days prior to treatment. Mice were treated 3 times a week for 14 days with an antibody targeting the αvβ3 binding RGDKGE (SEQ ID NO. 1) containing collagen epitope. Tumor sections were analyzed for expression of the immune checkpoint regulatory protein PDL-1 by immunofluorescence staining (FIG. 12).

Example 14

Enhanced Detection of Lymphocytic Infiltrates in Melanoma Tumors in Mice Treated with an Antibody Targeting the αvβ3 Ligand (RGDKGE (SEQ ID NO. 1) Containing XL313 Collagen Epitope)

Figure 13:
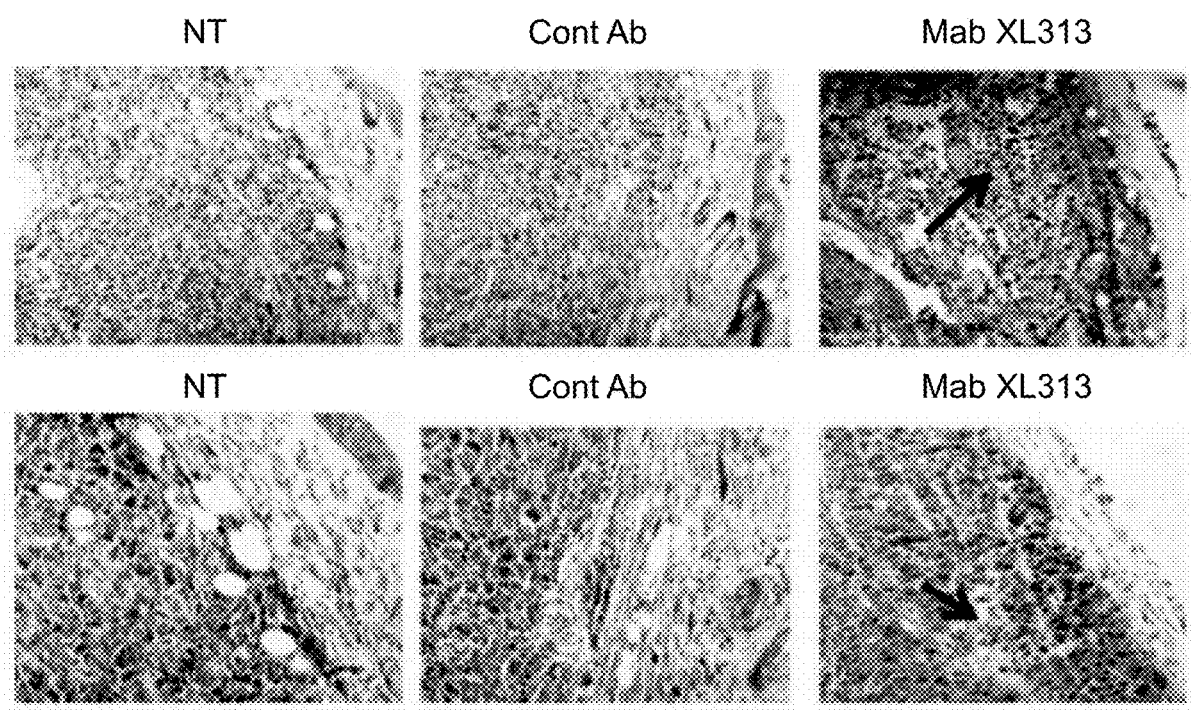
FIG. 13 are images depicting enhanced detection of lymphocytic infiltrates in melanoma tumors in mice treated with an antibody targeting the αvβ3 ligand (RGDKGE (SEQ ID NO. 1) containing XL313 collagen epitope). Mice (C57BL/6) were injected with 3.5×10⁵ B16F10 melanoma cells. Mice were allowed to establish pre-existing tumors for 5 days prior to treatment. Mice were treated (100 μg/mouse) 3 times a week for 14 days with an antibody targeting the αvβ3 binding RGDKGE (SEQ ID NO. 1) containing collagen epitope. Mice were sacrificed and tumors dissected. Tumor sections were analyzed for expression of the immune checkpoint regulatory protein PDL-1 by Giemsa staining. Black arrows indicate examples of areas with enhanced lymphocytic infiltrates.

Mice were injected with melanoma cells and were allowed to establish pre-existing tumors for 5 days prior to treatment. Mice were treated 3 times a week for 14 days with an antibody targeting the αvβ3 binding RGDKGE (SEQ ID NO. 1) containing collagen epitope (FIG. 13). Tumor sections were analyzed for expression of the immune checkpoint regulatory protein PDL-1.

Example 15

Detection of Enhanced Levels of PDL-1 Protein in Melanoma and Endothelial Cells Following Binding to 3 ECM Ligand (Denatured Collagen-IV)

Figure 14A:
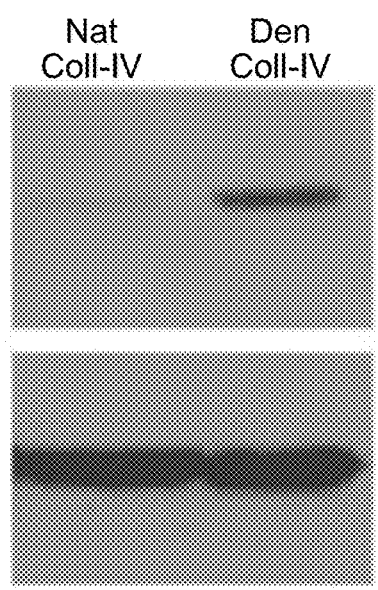
FIGS. 14A-14C are blots depicting detection of enhanced levels of PDL-1 protein in melanoma and endothelial cells following binding to αvβ3 ECM ligand (denatured collagen-IV).
Figure 14B:
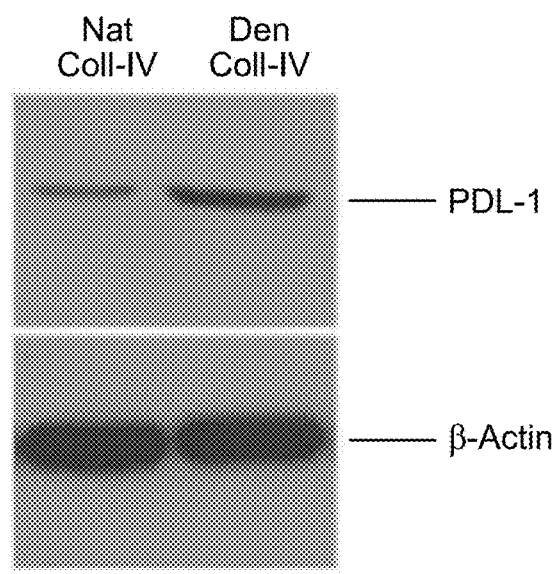
Figure 14C:
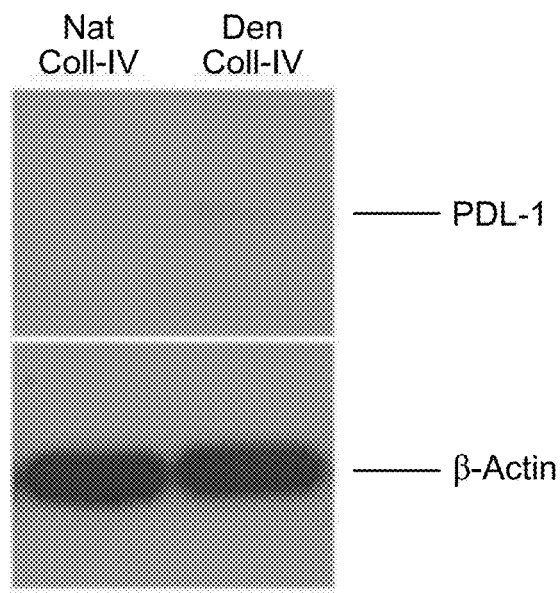

Integrin αvβ3 expressing melanoma cells M21 (FIG. 14A) and CCL-49 (FIG. 14B) and endothelial cells (HU-VEC) (FIG. 14C) were attached to wells coated with either a non-αvβ3 binding ligand (native collagen-IV) or an αvβ3 binding ligand (denatured collagen-IV). Whole cell lysates were prepared and the relative levels of PDL-1 or β-actin loading control were assessed.

Example 16

Enhanced Levels of PDL-1 Protein in Melanoma Cells Following Binding to αvβ3 Ligand XL313 Epitope (RGDKGE (SEQ ID NO. 1))

Figure 15:
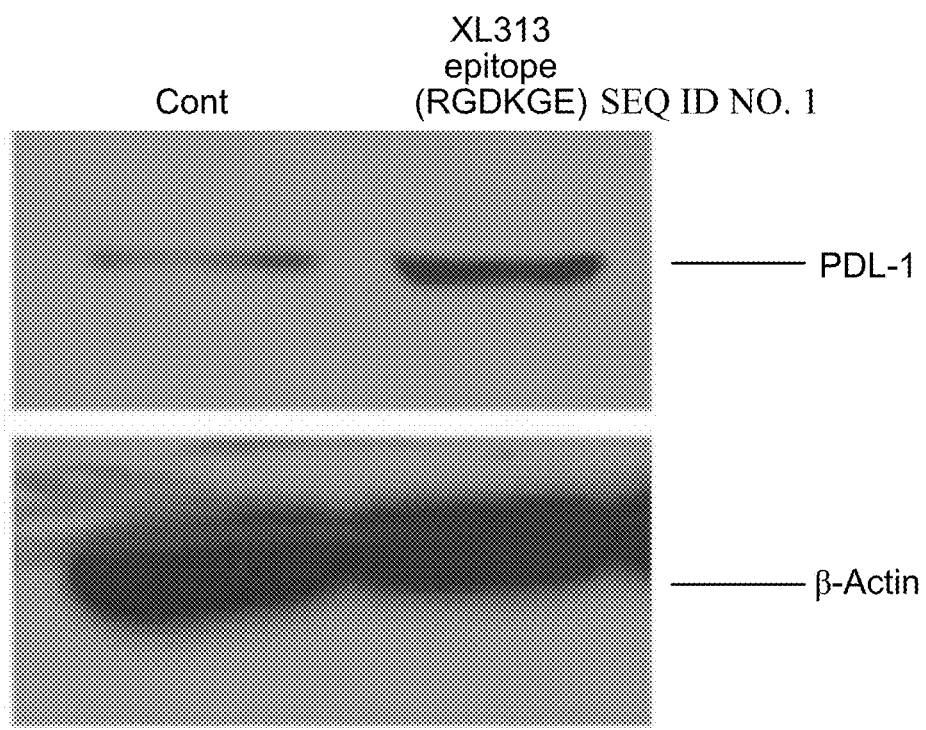
FIG. 15 is a blot depicting enhanced levels of PDL-1 protein in melanoma cells following binding to αvβ3 ligand XL313 epitope (RGDKGE (SEQ ID NO. 1)). Integrin αvβ3 expressing melanoma cells (M21) were seeded on control uncoated wells or wells immobilized with the XL313 cryptic collagen epitope (RGDKGE (SEQ ID NO. 1)). Following a 15 minute incubation cell lysates were prepared. The relative levels of PDL-1 or loading control β-actin were assessed by Western blot.

Integrin αvβ3 expressing melanoma cells (M21) were seeded onto control uncoated wells or wells immobilized with the XL313 cryptic collagen epitope (RGDKGE (SEQ ID NO. 1)) (FIG. 15). Following an incubation period, cell lysates were prepared and relative levels of PDL-1 were assessed.

Example 17

Reduction in the Levels of PDL-1 Protein in Melanoma Cells Following Blocking Binding to αvβ3 ECM Ligand (Denatured Collagen-IV) with a αvβ3 Specific Antibody LM609

Figure 16:
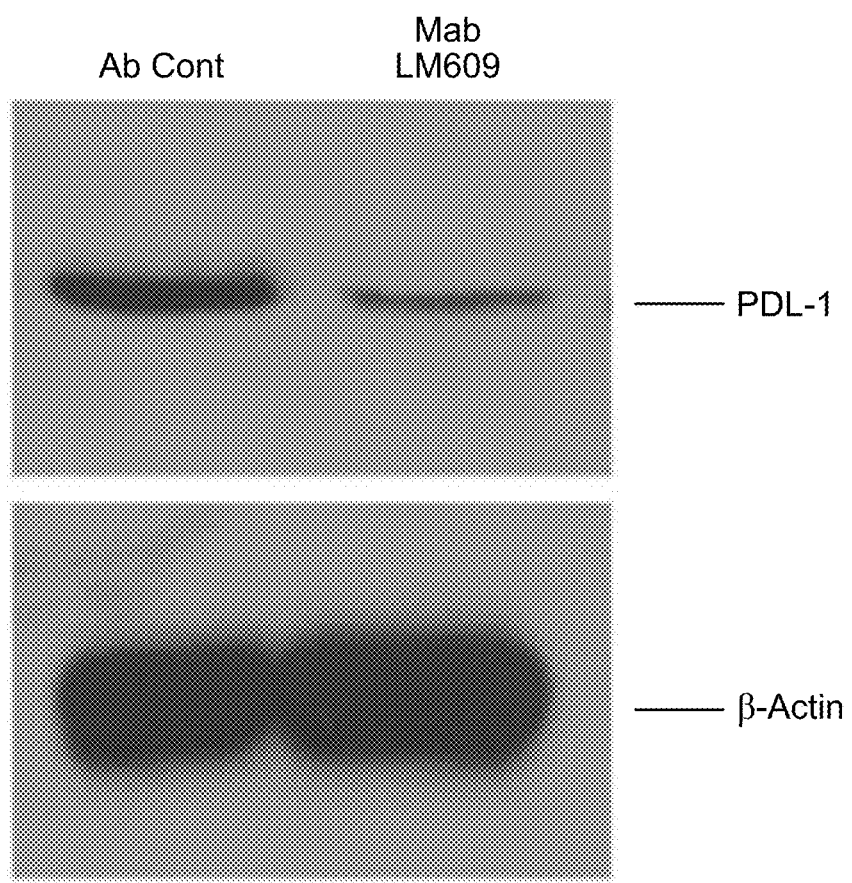
FIG. 16 is a blot depicting a reduction in the levels of PDL-1 protein in melanoma cells following blocking binding to αvβ3 ECM ligand (denatured collagen-IV) with a αvβ3 specific antibody LM609. Integrin αvβ3 expressing melanoma cells (M21) were mixed with a control non-specific (normal mouse Ig) or αvβ3 specific antibody (Mab LM609) and added to wells coated with the αvβ3 binding ligand (denatured collagen-IV). Whole cell lysates were prepared following a 24 hour incubation period and the relative levels of PDL-1 or loading control β-actin were assessed by Western blot.

Integrin αvβ3 expressing melanoma cells (M21) were mixed with a control non-specific (normal mouse Ig) or αvβ3 specific antibody (Mab LM609) and was added to wells coated with αvβ3 binding ligand (denatured collagen-IV) (FIG. 16). Whole cell lysates were prepared following a 24 hour incubation period and the relative levels of PDL-1 or loading control were assessed.

REFERENCES CITED

1. Bergers, G., and Hanahan, D. (2008) Modes of resistance to anti-angiogenic therapy. Nat. Rev. Cancer. 8, 593-604

2. Chung, A. S., Lee, J., and Ferrara, N. (2010) Targeting the tumor vasculature: insight from physiological angiogenesis. Nat. Rev. Cancer. 10, 505-514

3. Cao, Y., Arbiser, J., D'Amato, R. J., D'Amore, P. A., Ingber, D. E., Kerbel, R., Klagsburn, M., Lim, S., Moses, M. A., Zetter, B., Dvorak, H., and Langer, R. (2011) Forty-year journey of angiogenesis translational research. Sci. Transl. Med. 3, 114rv3

4. Contois, L., Akalu, A., and Brooks, P. C. (2009) Integrins as functional hubs in the regulation of pathological angiogenesis. Sem. Can. Biol. 19, 318-328

5. Moserle, L., Jimenz-Valerio, G., and Casanovas, O. (2014) Antiangiogenic therapies: going beyond their limits. Can. Discov. 4, 31-41

6. Greenberg, J. I., Shields, D. J., Barillas, S. G., Acevedo, L. M., Murphy, E., Huang, J., Scheppke, L., Stockmann, C., Johnson, R. S., Angle, N., and Cheresh, D. A. (2008) A role for VEGF as a negative regulator of pericyte function and vessel maturation. Nature. 456, 809-813

7. Hodivala-Dilke, K. (2008) αvβ3 integrin and angiogenesis: a moody integrin in a changing environment. Curr. Opin. Cell. Biol. 20, 514-519

8. Atkinson, S. J., Ellison, T. S., Steri, V., Gould, E., and Robinson, S. D. (2014) Redefining the role(s) of endothelial αvβ3-integrin in angiogenesis. Biochem. Soc. Trans. 42, 1590-1595

9. Robinson, S. D., and Hodivala-Dilke, K. H. (2011) The role of β3-integrins in tumor angiogenesis: context is everything. Curr. Opin. Cell. Biol. 23, 630-637

10. Brooks, P. C., Clark, R. A., and Cheresh, D. A. (1994) Requirement of vascular integrin alpha v beta 3 for angiogenesis. Science. 264, 569-571

11. Brooks, P. C., Montgomery, A. M., Rosenfeld, M., Reisfeld, R. A., Hu, T., Klier, G., and Cheresh, D. A. (1994) Integrin αvβ3 antagonists promote tumor regression by inducing apoptosis of angiogenic blood vessels. Cell. 79, 1157-1164

12. Contois, L. W., Akalu, A., Caron, J. M., Tweedie, E., Cretu, A., Henderson, T., Liaw, L., Friesel, R., Vary, C., and Brooks, P. C. (2014) Inhibition of tumor-associated αvβ3 integrin regulates the angiogenic switch by enhancing expression of IGFBP-4 leading to reduced melanoma growth and angiogenesis in vivo. Angiogenesis.

13. Reynolds, L. E., Wyder, L., Lively, J. C., Robinson, S. D., Huang, X., Sheppard, D., Hynes, R. O., and Hodivala-Dilke, K. M. (2002) Enhanced pathological angiogenesis in mice lacking beta 3 integrin or beta 3 and beta 5 integrins. Nat. Med. 8, 27-34

14. Feng, W., McCabe, N. P., Mahabeleshwar, G. H., Somanah, P. R., Phillips, D. R., and Byzova, T. (2008) The angiogenic response is dictated by β3 integrin on bone marrow-derived cells. J. Cell. Biol. 183, 1145-1157

15. Steri, V., Ellison, T. S., Gontarczyk, A. M., Weilbaecher, K., Schneider, J. G., Edwards, D., Fruttiger, M., Hodivala-Dilke, K. M., and Robinson, S. D. (2014) Acute depletion of endothelial β3-integrin transiently inhibits tumor growth and angiogenesis in mice. Cir. Res. 114, 79-91

16. Gong, Y., Yang, X., He, Q., Gower, L., Prudovsky, I., Vary, C. P. H., Brooks, P. C., and Friesel, R. E. (2013) Sprouty4 regulates endothelial cell migration via modulating integrin β3 stability through c-Src. Angiogenesis. 16, 861-875

17. Adair-Kirk, T. L., and Senior, R. M. (2008) Fragments of extracellular matrix as mediators of inflammation. Int. J. Biochem. Cell. Biol. 40, 1101-1110

18. Davis, G. E. (2011) Angiogenesis and proteinases: influence on vascular morphogenesis, stabilization and regression. Drug. Discov. Today. Dis. Models. 8, 13-20

19. Petitclerc, E., Boutaud, A., Prestayko, A., Xu, J., Sado, Y., Ninomiya, Y., Sarras, M. P., Hudson, B. G., and Brooks, P. C. (2000) New functions for non-collagenous domains of human collagen type-IV: novel integrin ligands inhibiting angiogenesis and tumor growth in vivo. J. Biol. Chem. 275, 8051-8061

20. Sudhakar, A., Sugimoto, H., Yang, C., Lively, J., Zeisberg, M., and Kalluri, R. (2003) Human tumstatin and endostatin exhibit distinct antiangiogenic activities mediated by αvβ3 and α5β1 integrins. Proc. Natl. Acad. Sci. USA. 100, 4766-4771

21. Xu, J., Petitclerc, E., Kim, J. J., Hangai, M., Moon, Y. S., Davis, G. E., and Brooks, P. C. (2001) Proteolytic exposure of a cryptic site within collagen type-IV is required for angiogenesis and tumor growth in vivo. J. Cell Biol. 154, 1069-1079

22. Hangai, M., Kitaya, N., Xu, J., Chan, C. K., Kim, J. J., Werb, Z., Ryan, S. J., and Brooks, P. C. (2002) Matrix metalloproteinase-9-dependent exposure of a cryptic migratory control site in collagen is required before retinal angiogenesis. Am. J. Pathol. 161, 1429-1437

23. Cretu, A., Roth, J. M., Caunt, M., Akalu, A., Policarpio, D., Formenti, S., Gagne, P., Liebes, L., and Brooks, P. C. (2007) Disruption of endothelial cell interactions with the novel HU177 cryptic collagen epitope inhibits angiogenesis. Clin. Cancer. Res. 15, 3068-3078

24. Pierschbacher, M. D., and Ruoslahti, E. (1987) Influence of stereochemistry of the sequence Arg-Gly-Asp-Xaa on binding specificity in cell adhesion. J. Biol. Chem. 262, 1729-1798

25. Kunicki, T. J., Annis, D. S., and Felding-Haberman. (1997) Molecular determinants of Arg-Gly-Asp ligand specificity for β3 integrins. J. Biol. Chem. 272, 4103-4107

26. Gurrath, M., Muller, G., Kessler, H., Aumilley, M., and Timpl. (1992) Conformational/activity studies of rationally designed potent anti-adhesive RGD peptides. Eur. J. Biochem. 210, 911-921

27. Kostidis, S., Stavrakoudis, A., Biris, N., Tsoukatos, D., Sakarellos, C., and Tsikaris, V. (2004) The relative orientation of the Arg and Asp side chains defined by a pseudodihedral angle as a key criterion for evaluating the structure-activity relationship of RGD peptides. J. Peptide. Sci. 10, 494-509

28. Miyoshi, T., Hirohata, S., Ogawa, H., Doi, M., Obika, M., Yonezawa, T., Sado, Y., Kusachi, S., Kyo, S., Kondo, S., Shiratori, Y., Hudson, B. G., and Ninomiya, Y. (2006) Tumor-specific expression of the RGD-α3(IV)NC1 domain suppresses endothelial tube formation and tumor growth in mice. FASEB. J. 20, 1264-1275

29. Danhier, F., Breton, A. L., and Preat, V. (2012) RGD-based strategies to target alpha (v) beta (3) integrin in cancer therapy and diagnosis. Mol. Pharmaceutics. 9, 2961-2973

30. Reynolds, A. R., Hart, I. R., Watson, A. R., Welti, J. C., Silva, R., Robinson, S. D., Violante, G. D., Gouraouen, M., Salih, M., Jones, M. C., Jones, D. T., Sunders, G., Kostourou, V., Perron-Sierra, F., Norman, J. C., Tucker, G. C., and Hodivala-Dilke, K. M. (2009) Stimulation of tumor growth and angiogenesis by low concentrations of RGD-mimetic integrin inhibitors. Nat. Med. 15, 392-400

31. Stupp, R., Hegi, M. E., Gorlia, T., Erridge, S. C., Perry, J., Hong, Y-K., Aldape, K. D., Lhermitte, B., Pietsch, T., Grujicic, D., Steinbach, J. P., Wick, W., Tarnawski, R., 31. Nam, D-H., Hau, P., Weyerbrock, A., Taphoon, M. J. B., Shen, C-C., Rao, N., Thurzo, L., Herrlinger, U., Gupta, T., Kortmann, R. D., Adamska, K., McBain, C., Brandes, A. A., Tonn, J. C., Schnell, O., Wiegel, T., Kim, C-Y., Nabors, L. B., Readon, D. A., van den Bent, M. J., Hicking, C., Markivsky, A., Picard, M., and Weller, T. (2014) Cilengitide combined with standard treatment for patients with newly diagnosed glioblastoma with methylated MGMT promoter (CENTRIC EORTC 26071-22072 study): a multicenter, randomized, open-label, phase 3 trial. Lancet. 15, 1100-11008

32. Blasi, E., Barluzzi, R., Bocchini, V., Mazzolla, R., and Bistoni, F. (1990) Immortalization of murine microglial cells by a v-raf/v-myc carrying retrovirus. J. Neuroimmun. 27, 229-237

33. Rouslahti, E. (1996) RGD and other recognition sequences for integrins. Annu. Rev. Cell Biol. 12, 697-715

34. Montgomery, A. M., Reisfeld, R. A., and Cheresh, D. A. (1994) Integrin alpha v beta 3 rescues melanoma cells from apoptosis in three-dimensional dermal collagen. Proc. Natl. Acad. Sci. USA. 91, 8856-8860

35. Madsen, D. H., Leonard, D., Masedunskas, A., Mayer, A., Jurgensen, H. J., Peters, D. E., Amornphimoltham, P., Selvaraj, A., Yamada, S. S., Brenner, D. A., Burgdorf, S., Engelholm, L. H., Behrendt, N., Holmbeck, K., Weigert, R., and Bugge, T. H. (2013) M2-like macrophages are responsible for collagen degradation through a mannose receptor-mediated pathway. J. Cell. Biol. 202, 951-966

36. Zwadlo-Klarwasser, G., Gorlitz, K., Hafemann, B., Klee, D., and Klosterhalefen, B. (2001) The chorioallantoic membrane of the chick embryo as a simple model for the study of the angiogenic and inflammatory response to biomaterials. J. Mater. Sci. Mater. Med. 12, 195-199

37. Deryugina, E. I., and Quigley, J. P. (2008) Chick embryo chorioallantoic membrane models to quantify angiogenesis induced by inflammatory and tumor cells or purified effector molecules. Meth. Enzymol. 444, 21-41

38. Skjot-Arkil, H., Barascuk, N., Register, T., and Karsdal, M. (2010) Macrophage-mediated proteolytic remodeling of the extracellular matrix in atherosclerosis results in neoepitopes: a potential new class of biochemical markers. Drug. Dev. Technol. DOI: 10.1089/adt.2009.0258

39. Rajashekhar, G., Kamocka, M., Marin, A., Suckow, M. A., Wolter, W. R., Badve, S., Sanjeevaiah, A. R., Pumiglia, K., Rosen, E., and Clauss, M. (2010) Pro-inflammatory angiogenesis is mediated by p38 MAP Kinase. J. Cell Physiol. DOI: 10.1002/jcp22404

40. Matsumoto, T., Turesson, I., Book, M., Gerwins, P., and Claesson-Welsh, L. (2002) p38 MAP Kinase negatively regulates endothelial cell survival, proliferation, and differentiation in FGF-2 stimulated angiogenesis. J. Cell. Biol. 156, 149-160

41. Contois, L. W., Nugent, D. P., Caron, J. M., Cretu, A., Tweedie, E., Akalu, A., Liebes, L., Friesel, R., Rosen, C., Vary, C., and Brooks, P. C. (2012) Insulin-like growth factor binding protein-4 differentially inhibits growth factor-induced angiogenesis. J. Biol. Chem. 287, 1779-1789

42. Mitra, S. K., and Schlaepfer, D. D. (2006) Integrin-regulated FAK-Src signaling in normal and cancer cells. Curr. Opin. Cell Biol. 18, 516-523

43. McMullen, M., Keller, R., Sussman, M., and Pumiglia, K. (2004) Vascular endothelial growth factor-mediated activation of p38 is dependent upon Src and RAFTK/Pyk2. Oncogene. 23, 1275-1282

44. Rousseau, S., Houle, F., Landry, J., and Huot, J. (1997) p38 MAP kinase activation by vascular endothelial growth factor mediates actin reorganization and cell migration in human endothelial cells. Oncogene. 15, 2169-2177

45. Alghisi, G. C., Ponsonnet, L., and Ruegg, C. (2009) The integrin antagonist cilengitide activates $\alpha v\beta 3$, disrupts VE-cadherin localization at cell junctions and enhances permeability in endothelial cells. Plose. One. 4, e449

46. Dupont, S., Morsut, L., Aragona, M., Enzo, E., Giulitti, S., Cordenonsi, M., Zanconato, F., Le Digabel, J. Forcato, M., Bicciato, S., Elvassore, N., and Piccolo, S. (2011) Role of YAP/TAZ in mechanotransduction Nature. 474, 179-183

47. Shen, Z., and Stanger, B. Z. (2015) YAP regulates S-phase entry in endothelial cells. Plose One. DOI: 10.1371/journal.pone.0117522

48. Dai, X., She, P., Chi, F., Feng, Y., Liu, H., Jin, D., Zhao, Y., Guo, X., Jiang, D., Guan, K-L., Zhong, T. P., and Zhao, B. (2013) Phosphorylation of angiomotin by Lats1/2 kinase inhibits F-actin binding, cell migration and angiogenesis. J. Biol. Chem. 288, 34041-34051

49. Adler, J. J., Johnson, D. E., Heller, B. L., Bringman, L. R., Ranahan, W. P., Conwell, M. D., Sun, Y., Hudman, A., and Wells, C. D. (2013) Serum deprivation inhibits the transcriptional co-activators YAP and cell growth via phosphorylation of the 130-Kda isoform of angiomotin by the LATS1/2 protein kinase. Proc. Natl. Acad. Sci. USA. 110, 17368-17373

50. Johnson, R., and Halder, G. (2014) The two faces of hippo: targeting the hippo pathway for regenerative medicine and cancer treatment. Nat. Rev. Drug. Discov. 13, 63-79

51. Brooke, B. S., Karnik, S. K., and Li, D. Y. (2003) Extracellular matrix in vascular morphogenesis and disease: structure versus signal. Trend. Cell. Biol. 13, 51-56

52. Bonnans, C., Chou, J., and Werb, Z. (2014) Remodeling the extracellular matrix in development and disease. Nat. Rev. Mol. Cell Biol. 15, 786-801

53. Pickup, M. W., Mouw, J. K., and Weaver, V. M. (2014) The extracellular matrix modulates the hallmarks of cancer. EMBO Reports. DOI: 10.15252/embr.201439246

54. Yip, K-P., and Marsh, D. J. (1997) An Arg-Gly-ASP peptide stimulates constriction in rat afferent arteriole. Am. J. Physiol. 273, 768-776

55. Mogford, J. E., Davis, G. E., Platts, S. H., and Meininger, G. A. (1996) Vascular smooth muscle alpha v beta 3 integrin mediates arteriolar vasodilation in response to RGD peptides. Cir. Res. 79, 821-826

56. Du, X., Plow, E. F., Frelinger, A. L., O'Toole, T. E., Loftus, J. C., and Ginsberg, M, H. (1991) Ligands activate integrin $\alpha IIb\beta 3$ (Platelet GPIIb-IIIa). Cell. 65, 409-416

57. Legler, D. FD., Wiedle, G., Ross, P. F., and Imhof, B. A. (2001) Superactivation of integrin $\alpha v\beta 3$ by low antagonists concentrations. J. Cell. Sci. 114, 1545-1553

58. Deryugina, E. I., Zajac, E., Juncker-Jensen, A., Kupriyanova, T. A., Welter, L., and Quigley, J. P. (2014) Tissue-infiltrating neutrophils constitute the major in vivo source of angiogenesis-inducing MMP-9 in the tumor microenvironment. Neoplasia. 16, 771-788

59. Schnoor, M., Cullen, P., Lorkowski, J., Stolle, K., Robenek, H., Troyer, D., Rauterberg, J., and Lorkowski, S. (2008) Production of type VI collagen by human macrophages: a new dimension in macrophage functional heterogenicity. J. Immunol. 180, 5707-5719

60. Jetten, N., Verbruggen, S., Gijbels, M. J., Post, M. J., De Winther, M. P. J., Donners, M. M. P. (2014) Anti-inflammatory M2, but not pro-inflammatory M1 macrophage promote angiogenesis in vivo. Angiogenesis. 17, 109-118

61. Shen, B., Delaney, M. K., and Du, X. (2012) Inside-out, outside-in, and inside-outside-in: G protein signaling in integrin-mediated cell adhesion, spreading, and retraction. Curr. Opin. Cell. Biol. 24, 600-606
62. Gong, H., Shen, B., Flevaris, P., Chow, C., Lam, S., C-T., Voyno-Yasenetskaya, T. A., Kozasa, T., and Du, X. (2010) G-protein subunit Gα13 binds to integrin αIIbβ3 and mediates integrin outside-in signaling. Science. 327, 340-343
63. Liao, Z., Kato, H., Pandey, M., Cantor, J. M., Ablooglu, A. J., Ginsberg, M. H., and Shattil, S. J. (2015) Interaction of kindlin-2 with integrin β3 promotes outside-in signaling responses by the αvβ3 vitronectin receptor. Blood. Doi:10.1182/blood-2014-09-603035
64. Von Wichert, G., Jiang, G., Kostic, A., De Vos, K., Sap, J., and Sheetz, M. (2003) RPTP-α acts as a transducer of mechanical force on αvβ3-integrin-cytoskeleton linkage. J. Cell. Biol. 161, 143-153
65. Somanath, P. R., Malinin, N. L., and Byzova, T. V. (2009) Cooperation between integrin αvβ3 and VEGFR2 in angiogenesis. Angiogenesis. 12, 177-185
66. Yu, C-H., Law, J. B. K., Suryana, M., Low, H. Y., and Sheetz, M. P. (2011) Early integrin binding to Arg-Gly-Asp peptide activates actin polymerization and contractile movement that stimulates outward translocation. Proc. Natl. Acad. Sci. USA. 108, 20585-20590
67. Tang, Y., Rowe, G., Botvinick, E. L., Kurup, A., Putman, A. J., Seiki, M., Weaver, V. M., Keller, E. T., Goldstein, S., Dai, J., Begun, D., Saunders, T., and Weiss, S. J. (2013) MT1-MMP-dependent control of skeletal stem cell commitment via a β1-integrin/YAP/TAZ signaling axis. Dev. Cell. 25, 402-416
68. Kaneko, K., Ito, M., Naoe, Y., Lacy-Hulbert, A., and Ikeda, K. (2014) Integrin αv in the mechanical response of osteoblast lineage cells. Biochem. Biophys. Res. Commun. 447, 352-357

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

We claim:

1. A method of treating melanoma in a subject comprising, identifying a subject that has been diagnosed with melanoma;

administering an immune checkpoint inhibitor, wherein the immune checkpoint inhibitor comprises a PDL-1 antibody;

administering an antagonist of denatured collagen or a fragment thereof, wherein the antagonist of denatured collagen comprises an antagonist of the XL313 cryptic collagen epitope, wherein the antagonist comprises the XL313 monoclonal antibody deposited with ATCC accession number PTA-8552, and thereby treating melanoma in said subject.

2. The method of claim 1, wherein said antagonist of collagen or a fragment thereof enhances anti-tumor activity of the immune checkpoint inhibitor.

3. The method of claim 1, wherein the XL313 monoclonal antibody binds a cryptic RGDKGE (SEQ ID NO. 1) containing collagen epitope.

4. The method of claim 1, wherein the subject is a human.

5. The method of claim 1, further comprising administering a chemotherapy agent.

6. The method of claim 1, wherein said immune checkpoint inhibitor is administered at a dose of 0.01-10 mg/kg bodyweight, and wherein said antagonist of collagen is administered at a dose of 0.01-25 mg/kg bodyweight.

* * * * *

UNITED STATES PATENT AND TRADEMARK OFFICE
CERTIFICATE OF CORRECTION

PATENT NO. : 10,881,732 B2
APPLICATION NO. : 15/169863
DATED : January 5, 2021
INVENTOR(S) : Peter C. Brooks et al.

It is certified that error appears in the above-identified patent and that said Letters Patent is hereby corrected as shown below:

In the Claims

At Column 47, Claim number 1, Line number 14, replace "PTA-8552" with --PTA-6552--

Signed and Sealed this
Twenty-fifth Day of June, 2024

*Katherine Kelly Vidal*

Katherine Kelly Vidal
*Director of the United States Patent and Trademark Office*

SEQUENCE LISTING

```
<160> NUMBER OF SEQ ID NOS: 15

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Arg Gly Asp Lys Gly Glu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Lys Gly Asp Arg Gly Asp Ala Pro Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Gln Gly Pro Arg Gly Asp Lys Gly Glu
1               5

<210> SEQ ID NO 4
```

-continued

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Gln Gly Pro Ser Gly Ser Pro Gly Glu
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide

<400> SEQUENCE: 5

Cys Lys Gly Asp Arg Gly Asp Ala Pro Gly Cys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

Cys Gln Gly Pro Arg Gly Asp Lys Gly Glu Cys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Cys Ala Gly Ser Arg Gly Asp Gly Gly Pro Cys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Cys Gln Gly Ile Arg Gly Asp Lys Gly Glu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

Cys Arg Gly Pro Arg Gly Asp Gln Gly Pro Cys
1               5                   10

<210> SEQ ID NO 10
<211> LENGTH: 11
```

```
<212> TYPE: PRT
<213> ORGANISM: Artificial Sequence
<220> FEATURE:
<223> OTHER INFORMATION: Synthetic peptide

<400> SEQUENCE: 10

Cys Gln Gly Pro Ser Gly Ala Pro Gly Glu Cys
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Arg Gly Asp Ala Pro Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Ala Gly Ser Arg Gly Asp Gly Gly Pro
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Gln Gly Ile Arg Gly Asp Lys Gly Glu
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Arg Gly Pro Arg Gly Asp Gln Gly Pro
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Gln Gly Pro Ser Gly Ala Pro Gly Glu
1               5
```